(12) United States Patent
Fang et al.

(10) Patent No.: US 9,693,874 B2
(45) Date of Patent: Jul. 4, 2017

(54) COMPOSITE SPINAL INTERBODY DEVICE AND METHOD

(71) Applicant: BLACKSTONE MEDICAL, INC., Lewisville, TX (US)

(72) Inventors: Samuel Fang, Plano, TX (US); Francesco Larosa, Neptune, NJ (US); James Klein, Dallas, TX (US)

(73) Assignee: Blackstone Medical, Inc., Lewisville, TX (US)

( * ) Notice: Subject to any disclaimer, the term of this patent is extended or adjusted under 35 U.S.C. 154(b) by 150 days.

(21) Appl. No.: 13/842,743

(22) Filed: Mar. 15, 2013

(65) Prior Publication Data

US 2014/0277491 A1 Sep. 18, 2014

(51) Int. Cl.
*A61F 2/44* (2006.01)
*A61F 2/46* (2006.01)
(Continued)

(52) U.S. Cl.
CPC .......... *A61F 2/4455* (2013.01); *A61F 2/447* (2013.01); *A61F 2/4465* (2013.01);
(Continued)

(58) Field of Classification Search
CPC .......... A61F 2/441; A61F 2310/00023; A61F 2002/30578; A61F 2002/30772;
(Continued)

(56) References Cited

U.S. PATENT DOCUMENTS 5,171,281 A 12/1992 Parsons et al.
5,732,469 A * 3/1998 Hamamoto .......... A61C 8/0012
29/896.6

(Continued)

OTHER PUBLICATIONS

International Search Report and Written Opinion, PCT/US2009/060545, dated Dec. 14, 2009, 11 pages.

(Continued)

*Primary Examiner* — Ellen C Hammond
*Assistant Examiner* — Tessa Matthews
(74) *Attorney, Agent, or Firm* — Baker & McKenzie LLP

(57) ABSTRACT

A composite interbody device for use with spinal fusion surgery is described herein. The composite interbody device comprises a central body made from a radiolucent biocompatible polymer (e.g., PEEK or UHMWPE) and metallic plates, which are placed at the superior and inferior surfaces of the central body. The metallic plates are comprised of an end plate that is adjacent to a vertebral body and an intermediate plate that is adjacent to the central body. The end plates may have one or more arrays of apertures to facilitate bone growth into the end plates to secure the interbody device within the intervertebral space. The intermediate plates may also have one or more arrays of apertures to allow the central body to bond to the end plates through compression molding, injection molding, and/or heat molding. The arrays of apertures in the end plates are not aligned with the arrays of apertures in the intermediate plates so that polymer material of the central body will not penetrate into the end plate, where bone growth is encouraged, and vice versa.

31 Claims, 16 Drawing Sheets

(51) Int. Cl.
*A61B 17/80* (2006.01)
*A61F 2/30* (2006.01)

(52) U.S. Cl.
CPC ......... *A61F 2/4611* (2013.01); *A61B 17/8042* (2013.01); *A61F 2002/30004* (2013.01); *A61F 2002/30011* (2013.01); *A61F 2002/3093* (2013.01); *A61F 2002/30143* (2013.01); *A61F 2002/30156* (2013.01); *A61F 2002/30172* (2013.01); *A61F 2002/30388* (2013.01); *A61F 2002/30599* (2013.01); *A61F 2002/30785* (2013.01); *A61F 2002/30787* (2013.01); *A61F 2002/30789* (2013.01); *A61F 2002/30808* (2013.01); *A61F 2002/30841* (2013.01); *A61F 2002/30922* (2013.01); *A61F 2002/30957* (2013.01); *A61F 2002/30971* (2013.01); *A61F 2002/4475* (2013.01); *A61F 2002/4623* (2013.01); *A61F 2002/4627* (2013.01)

(58) Field of Classification Search
CPC .... A61F 2002/30784; A61F 2002/3082; A61F 2002/3092
USPC ...................................................... 623/17.16
See application file for complete search history.

(56) References Cited

U.S. PATENT DOCUMENTS

| | | | |
|---|---|---|---|
| 6,533,818 | B1 | 3/2003 | Weber et al. |
| 6,607,558 | B2 | 8/2003 | Kuras |
| 6,863,689 | B2 | 3/2005 | Ralph et al. |
| 6,994,727 | B2 | 2/2006 | Khandkar et al. |
| 7,011,684 | B2 | 3/2006 | Eckman |
| 7,169,181 | B2 | 1/2007 | Kuras |
| 7,263,159 | B2 | 8/2007 | Russell |
| 8,262,737 | B2 | 9/2012 | Bagga et al. |
| 8,303,879 | B2 | 11/2012 | Bertele et al. |
| 8,361,150 | B2 | 1/2013 | Zhang et al. |
| 8,414,650 | B2 | 4/2013 | Bertele et al. |
| 8,414,820 | B2 | 4/2013 | Bertele et al. |
| 2004/0010313 | A1 | 1/2004 | Aston et al. |
| 2005/0112397 | A1* | 5/2005 | Rolfe ................. A61B 17/8605 428/593 |
| 2005/0149026 | A1 | 7/2005 | Butler et al. |
| 2005/0271694 | A1 | 12/2005 | Mansouri et al. |
| 2006/0173542 | A1 | 8/2006 | Shikinami |
| 2006/0241764 | A1 | 10/2006 | Michelson |
| 2007/0043442 | A1 | 2/2007 | Abernathie et al. |
| 2008/0101908 | A1 | 5/2008 | Bao et al. |
| 2008/0103598 | A1 | 5/2008 | Trudeau et al. |
| 2008/0249627 | A1 | 10/2008 | Moehlenbruck et al. |
| 2008/0306609 | A1* | 12/2008 | Lee et al. .................... 623/23.58 |
| 2009/0105831 | A1 | 4/2009 | Jones et al. |
| 2009/0164020 | A1 | 6/2009 | Janowski et al. |
| 2009/0326657 | A1 | 12/2009 | Grinberg et al. |
| 2010/0042218 | A1 | 2/2010 | Nebosky et al. |
| 2010/0075419 | A1* | 3/2010 | Inagaki ................... A61L 27/56 435/402 |
| 2010/0076559 | A1 | 3/2010 | Bagga et al. |
| 2010/0094426 | A1 | 4/2010 | Grohowski, Jr. et al. |
| 2010/0331986 | A1* | 12/2010 | Shikinami ................. 623/17.16 |
| 2011/0071635 | A1* | 3/2011 | Zhang et al. .............. 623/17.11 |
| 2011/0087327 | A1* | 4/2011 | Lechmann et al. ........ 623/17.11 |
| 2011/0190888 | A1* | 8/2011 | Bertele et al. ............. 623/17.11 |
| 2012/0172991 | A1 | 7/2012 | Bertele et al. |

OTHER PUBLICATIONS

International Search Report and Written Opinion, PCT/US2014/024771, dated Sep. 16, 2014, 17 pages.

Extended European Search Report, EP Application No. 14768629.9, dated Feb. 14, 2017, 9 pages.

\* cited by examiner

COMPOSITE SPINAL INTERBODY DEVICE AND METHOD

TECHNICAL FIELD

The present disclosure relates generally to a composite interbody device adapted for insertion between two adjacent vertebrae to promote the fusion of two vertebrae.

BACKGROUND

The bones and connective tissue of an adult human spinal column consists of more than 20 discrete bones coupled sequentially to one another by a tri-joint complex. The complex consists of an anterior disc and two posterior facet joints. The anterior discs of adjacent bones are cushioned by cartilage spacers referred to as intervertebral discs. The over 20 bones of the spinal column are anatomically categorized as one of four classifications: cervical, thoracic, lumbar, or sacral. The cervical portion of the spine which comprises the top of the spine up to the base of the skull, includes the first 7 vertebrae. The intermediate 12 bones are thoracic vertebrae, and connect to the lower spine comprising the 5 lumbar vertebrae. The base of the spine are sacral bones, including the coccyx.

The spinal column of bones is highly complex in that it includes over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction.

Genetic or developmental irregularities, trauma, chronic stress, tumors and disease, however, can result in spinal pathologies which either limit this range of motion or threaten the critical elements of the nervous system housed within the spinal column. A variety of systems have been disclosed in the art which achieve immobilization by implanting artificial assemblies in or on the spinal column. These assemblies may be classified as anterior, posterior or lateral implants. Lateral and anterior assemblies are coupled to the anterior portion of the spine which is in the sequence of vertebral bodies. Posterior implants generally comprise pairs of rods ("bilateral spinal support rods"), which are aligned along the axis which the bones are to be disposed, and which are then attached to the spinal column by either hooks which couple to the lamina or attach to the transverse processes, or by screws which are inserted through pedicles.

Spinal fusion treatment is commonly used to treat spinal disc disease and/or spinal instability. The degeneration of spinal discs can create significant pain and discomfort for individuals suffering from this affliction. In many cases, this pain can be alleviated by immobilizing the vertebrae adjacent to the degenerated disc and encouraging bone growth across the immobilized area of the spine. Conventional spinal implants are designed to facilitate bone through-growth, or fusion resulting from growth of bone through holes or channels through the implants. Although effective, the bone through-growth process is slow, sometimes taking more than a year to complete. Through-growth can be further delayed if the implant area is not immobilized. Even micro-motion of the implant area can disturb and disrupt bone growth, leading to increased incidence of subsidence and pseudarthrosis.

Some conventional devices attempt to improve implant stabilization by encouraging bone on-growth—a comparatively rapid, planar growth of bone upon surfaces of an adjacent implant, or upon surfaces of adjacent bone. For example, on-growth may be encouraged by coating a titanium cage with a chemical such as hydroxyapatite to encourage new-grown bone to adhere to the implant surface. However, because titanium is radioopaque, titanium implants can interfere with diagnostic assessment of bone growth, whether coated with hydroxyapatite or not. For example, implants made primarily of radio-opaque titanium may obscure visualization of bone growth (e.g., through-growth) on x-rays. Titanium may likewise cause signal artifact with MRIs or CTs, making it difficult to determine if fusion has occurred.

In order to avoid the visualization problems of titanium implants, attempts have been made to mix hydroxyapatite with, or apply hydroxyapatite to, radiolucent polymer plastics (e.g., PEEK, HDPE, or other non-scattering biocompatible materials) to form a cage/implant. However, PEEK provides poorer fixation than titanium, and thus, PEEK implants often require supplemental fixation such as posterior pedicle screws and rod instrumentation.

SUMMARY

Various embodiments of a composite interbody device for use with spinal fusion surgery are described herein. The composite interbody device may a central body made from a radiolucent biocompatible polymer (e.g., PEEK or UHMWPE) and metallic plates that are placed at the superior and inferior surfaces of the central body. The metallic plates comprise an end plate that is adjacent to a vertebral body and an intermediate plate that is adjacent to the central body. The end plates may have one or more arrays of apertures to facilitate bone growth into the end plates to secure the interbody device within the intervertebral space. The intermediate plates may also have one more arrays of apertures or linear recesses to allow the central body to bond to the end plates through compression molding, injection molding, and/or heat molding. The arrays of apertures in the end plates are not aligned with the arrays of apertures in the intermediate plates so that polymer material of the central body will not penetrate into the end plate, where bone growth is encouraged, and vice versa.

According to one embodiment, a composite interbody device may comprise a first end plate comprising a biocompatible metal and having a superior surface adapted to contact an upper vertebral body, an inferior surface, an exterior side wall connecting the superior surface to the inferior surface, and an interior side wall connecting the superior surface to the inferior surface, the first end plate further comprising an array of apertures passing from the superior surface to the inferior surface; a first intermediate plate comprising a biocompatible metal and having a superior surface adapted to contact the inferior surface of the first endplate, an inferior surface, an exterior side wall connecting the superior surface to the inferior surface, and an interior side wall connecting the superior surface to the inferior surface, the first intermediate plate further comprising an array of apertures passing from the superior surface to the inferior surface; a central body comprising a biocompatible polymer and having a superior surface adapted to contact the inferior surface of the first intermediate plate, an inferior surface, an exterior side wall connecting the superior surface to the inferior surface, and an interior side wall connecting the superior surface to the inferior surface; a second intermediate plate comprising a biocompatible metal and having a superior surface adapted to contact the inferior surface of the central body, an inferior surface, an exterior side wall connecting the superior surface to the inferior surface, and an interior side wall connecting the superior surface to the inferior surface, the second intermediate plate further comprising an array of apertures passing from the superior surface to the inferior surface; a second end plate comprising a biocompatible metal and having a superior surface adapted to contact the inferior surface of the second intermediate plate, an inferior surface adapted to contact a lower vertebral body, an exterior side wall connecting the superior surface to the inferior surface, and an interior side wall connecting the superior surface to the inferior surface, the second end plate further comprising an array of apertures passing from the superior surface to the inferior surface; wherein the array of apertures at the inferior surface of the first end plate do not overlap the array of apertures at the superior surface of the first intermediate plate when the inferior surface of the first end plate contacts the superior surface of the first intermediate plate; and wherein the array of apertures at the inferior surface of the second intermediate plate do not overlap the array of apertures at the superior surface of the second end plate when the inferior surface of the second intermediate plate contacts the superior surface of the second end plate.

According to another embodiment, a composite interbody device suitable for insertion between two adjacent vertebrae is formed according to the following method: forming a first end plate comprising a biocompatible metal and having a superior surface operable to contact a upper vertebral body, an inferior surface, an exterior side wall connecting the superior surface to the inferior surface, and an interior side wall connecting the superior surface to the inferior surface, the first end plate further comprising a first array of apertures passing from the superior surface to the inferior surface, a second array of apertures passing from the interior side wall to the exterior side wall, and a third array of apertures passing from another interior side wall to another exterior side wall, wherein the first, second, and third arrays of apertures intersect each other inside the first end plate; forming a first intermediate plate comprising a biocompatible metal and having a superior surface, an inferior surface, an exterior side wall connecting the superior surface to the inferior surface, and an interior side wall connecting the superior surface to the inferior surface, the first intermediate plate further comprising a fourth array of apertures passing from the superior surface to the inferior surface, a fifth array of apertures passing from the interior side wall to the exterior side wall, and a sixth array of apertures, passing from another interior side wall to another exterior side wall, wherein the fourth, fifth, and sixth arrays of apertures intersect each other inside the first intermediate plate; connecting the first end plate to the first intermediate plate so that the first array of apertures at the inferior surface of the first end plate do not overlap the third array of apertures at the superior surface of the first intermediate plate when the inferior surface of the first end plate; forming a second intermediate plate comprising a biocompatible metal and having a superior surface, an inferior surface, an exterior side wall connecting the superior surface to the inferior surface, and an interior side wall connecting the superior surface to the inferior surface, the second intermediate plate further comprising a seventh array of apertures passing from the superior surface to the inferior surface, an eighth array of apertures passing from the interior side wall to the exterior side wall, a ninth array of apertures, passing from another interior side wall to another exterior side wall, wherein the seventh, eighth, and ninth arrays of apertures intersect each other inside the second intermediate plate; forming a second end plate comprising a biocompatible metal and having a superior surface, an inferior surface operable to contact a lower vertebral body, an exterior side wall connecting the superior surface to the inferior surface, and an interior side wall connecting the superior surface to the inferior surface, the second end plate further comprising a tenth array of apertures passing from the superior surface to the inferior surface, an eleventh sixth array of apertures, passing from an interior side wall to an exterior side wall, and a twelfth array of apertures, passing from another interior side wall to another exterior side wall; connecting the second end plate to the second intermediate plate so that the seventh array of apertures at the inferior surface of the second intermediate plate does not overlap the tenth array of apertures at the superior surface of the second end plate; forming a central body comprising a biocompatible polymer and having a superior surface, an inferior surface, an exterior side wall connecting the superior surface to the inferior surface, and an interior side wall connecting the superior surface to the inferior surface; connecting the superior surface of the central body to the inferior surface of the first intermediate plate; and connecting the inferior surface of the central body to the superior surface of the second intermediate plate.

BRIEF DESCRIPTION OF THE DRAWINGS

For a more complete understanding of the present disclosure and its advantages, reference is now made to the following description taken in conjunction with the accompanying drawings, in which like reference numbers indicate like features, and.

Although similar reference numbers may be used to refer to similar elements for convenience, it can be appreciated that each of the various example embodiments may be considered to be distinct variations.

DETAILED DESCRIPTION

Exemplary embodiments will now be described hereinafter with reference to the accompanying figures, which form a part hereof, and which illustrate examples by which the exemplary embodiments, and equivalents thereof, may be practiced. As used in the disclosures and the appended claims, the terms "embodiment," "example embodiment" and "exemplary embodiment" do not necessarily refer to a single embodiment, although it may, and various example embodiments, and equivalents thereof, may be readily combined and interchanged, without departing from the scope or spirit of present embodiments. Furthermore, the terminology as used herein is for the purpose of describing example embodiments only and is not intended to be limitations of the embodiments. In this respect, as used herein, the term "plate" may refer to any substantially flat structure or any other three-dimensional structure, and equivalents thereof, including those structures having one or more portions that are not substantially flat along one or more axis. Furthermore, as used herein, the terms "opening," "recess," "aperture," and equivalents thereof, may include any hole, space, area, indentation, channel, slot, bore, and equivalents thereof, that is substantially round, oval, square, rectangular, hexagonal, and/or of any other shape, and/or combinations thereof, and may be defined by a partial, substantial or complete surrounding of a material surface. Furthermore, as used herein, the term "in" may include "in" and "on," and the terms "a," "an" and "the" may include singular and plural references. Furthermore, as used herein, the term "by" may also mean "from," depending on the context. Furthermore, as used herein, the term "if" may also mean "when" or "upon," depending on the context. Furthermore, as used herein, the words "and/or" may refer to and encompass any and all possible combinations of one or more of the associated listed items.

Figure 1:
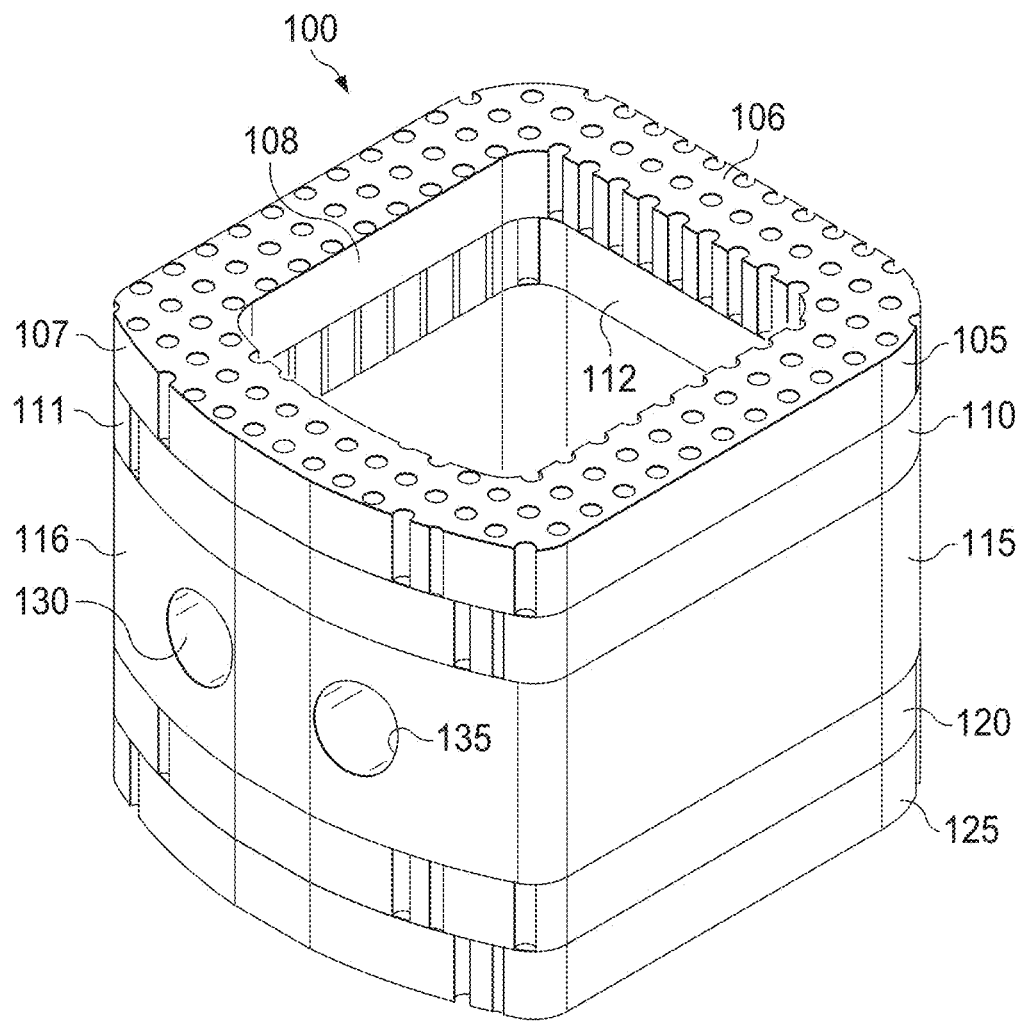
FIG. 1 is a perspective view of an exemplary embodiment of a composite interbody device, according to one aspect of the invention.

An embodiment consistent with one aspect of the invention is depicted in FIG. 1. In FIG. 1, a composite interbody device 100 is depicted as having multiple layers including a first end plate 105, a first intermediate plate 110, a central body 115, a second intermediate plate 120, and a second end plate 125. Preferably, the end plates (105, 125) and intermediate plates (110, 120) are comprised of a biocompatible metal such as surgical stainless steel or titanium. The first end 105 plate comprises a superior surface 106 that is adopted to be contacted to an upper vertebral body. The first end plate 105 also comprises an inferior surface (not visible) on an opposite side of the plate from the superior surface 106. The first end plate 105 also includes an exterior sidewall 107 that connects the superior surface 106 to the inferior surface and passes around the circumference of the inter body device 100. In addition, the first end plate 105 may include an interior sidewall 108 that connects the superior surface 106 to the inferior surface at the interior of the first end plate 105.

Also shown in FIG. 1 is a first intermediate plate 110 that comprises a superior surface that connects to the inferior surface of the first end plate 105. The first intermediate plate 110 also includes an inferior surface that is located on an opposite side from the superior surface. The first intermediate plate 110 further includes an exterior sidewall 111 that connects the superior surface to the inferior surface and extends around the circumference of the first intermediate plate 110. In addition, the first intermediate plate 110 also includes and interior sidewall 112 that extends from the superior surface of the first intermediate plate to the inferior surface of the first intermediate plate 110.

The composite inter-body device 100 also includes a central body 115 that is comprised of a biocompatible polymer such as Polyether-ether-ketone (PEEK) or Ultra High Molecular Weight Polyethylene (UHMWPE). It is preferable that the central body 115 be comprised of a material that is radiolucent so that the amount of bone on-growth and through-growth can be monitored through X-ray imaging. The central body 115 comprises a superior surface 117 that is adapted to contact these inferior surface of the first intermediate plate 110 and an inferior surface (not shown) that is adapted to contact to the superior surface 121 of the second intermediate plate 120 (see FIG. 1A). The central body 115 also includes an exterior side wall 116 and an interior side wall 118 that connect the superior surface of the central body 117 to the inferior surface of the central body. The central body 115 also comprises two holes 130 and 135 that are formed in the exterior side wall 116 and pass through the interior side wall 118. Holes 130 and 135 can be used with an implantation tool to insert the interbody device 100 into the space between two adjacent vertebrae. The use of these holes 130, 135 will be described in more detail with reference to FIGS. 14A-14C below.

In the embodiment depicted in FIG. 1, the composite interbody device 100 further comprises a second intermediate plate 120 and a second end plate 125 having similar surfaces and end walls to the first end plate 105 and first intermediate plate 110. The inferior surface (not shown) of the second end plate 125 is adapted to contact a lower vertebral body. Thus, when the composite interbody device 100 is inserted between two adjacent vertebrae, the two end plates (105, 125) will maintain contact with the surfaces of the adjacent vertebrae.

Figure 1A:
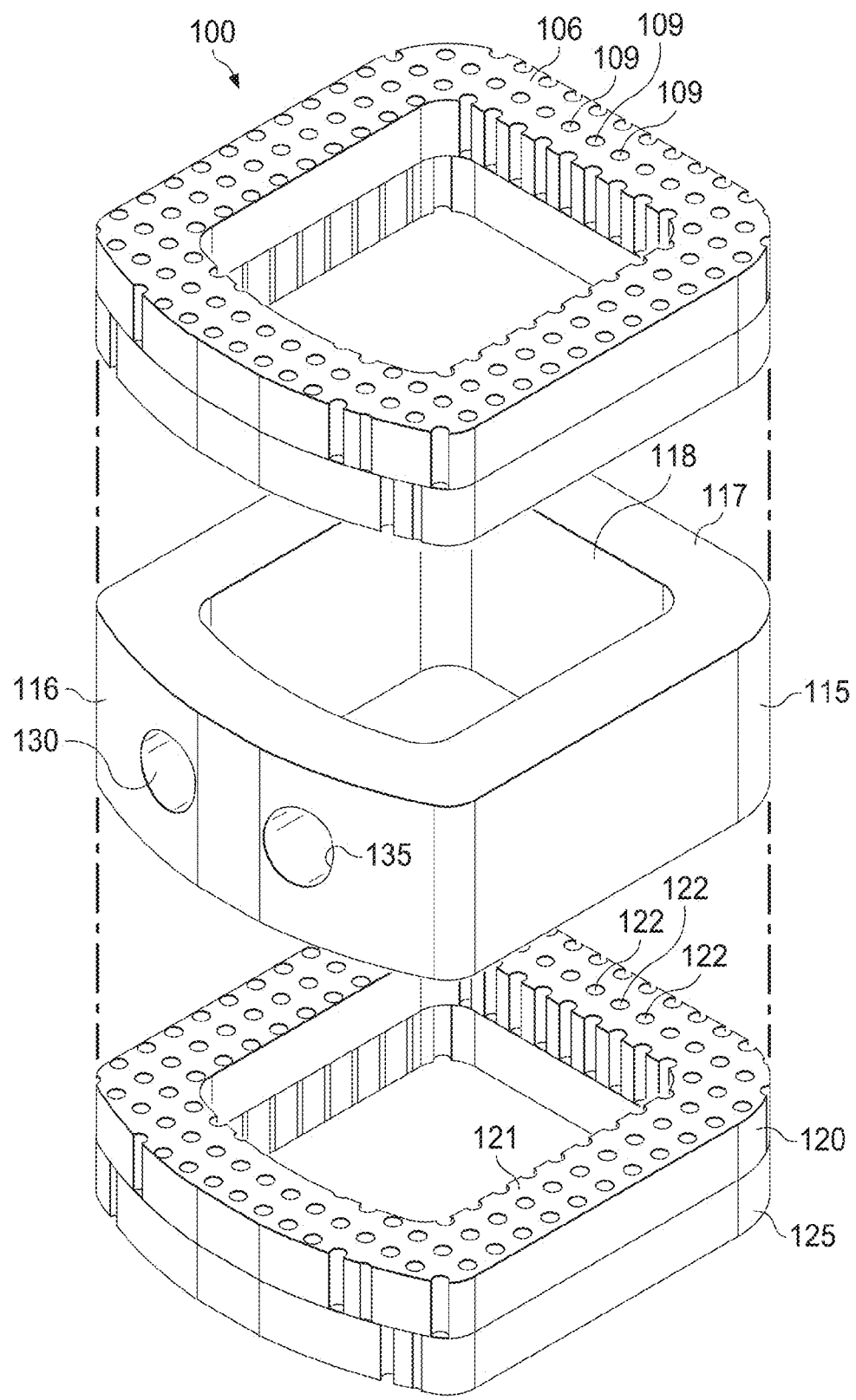
FIG. 1A is an exploded perspective view of an exemplary embodiment of a composite interbody device, according to one aspect of the invention.

An exploded view of the composite inter-body device 100 is depicted in FIG. 1A. As seen in FIG. 1A, the central body 115 includes a superior surface 117 that contacts the inferior surface of the first intermediate plate 110. Also shown in FIG. 1A is a superior surface 121 of the second intermediate plate 120 that is adopted to contact with the inferior surface of the central body 115.

Another feature of the composite interbody device 100 depicted in FIGS. 1 and 1A is the arrays of apertures that are found in the end plates (105, 125) and the intermediate plates (110, 120). The array of apertures in the first end plate 105 comprises a series of holes 109 that pass through the first end plate from its superior surface 106 to its inferior surface. Although the apertures 109 depicted in FIGS. 1 and 1A have a circular cross-section, other apertures may be utilized, including, apertures having a square, rectangular, elliptical, hexagonal, triangular, or any other cross-section that can be readily formed in the end plate according to known fabrication processes. Preferably, the apertures in the first end plate 105 must be of a sufficient size to permit bone in-growth, on-growth, and through-growth in the first end plate 105. In addition, the array of apertures 109 formed on the superior surface of the first end plate 105 form a frictional surface that discourages relative movement of the composite interbody device 100 with respect to the adjacent vertebral body. Spikes or ridges can be incorporated into the superior surface 106 of the first end plate 105 (and on the inferior surface of the second end plate 125) to further restrict the relative movement of the composite interbody device 100 with respect to the adjacent vertebral body. Although not visible in FIG. 1 or 1A, the second end plate 125 may comprise an array of apertures from the superior surface 121 to the inferior surface of the second end plate 125. Like the first end plate 105, this array of apertures creates a frictional surface on the inferior surface of the second end plate 125 that discourages relative movement of the composite interbody device 100 with respect to the lower adjacent vertebral body. Further, the array of apertures in the second end plate 125 must be of a sufficient size to permit bone in-growth, on-growth, and through-growth in the second end plate 125. Both the first intermediate plate 110 and the second intermediate plate 120 include arrays of apertures that are similar to the arrays of apertures found in the first end plate 105 and second end plate 120. According to one embodiment, the arrays of apertures in the end plates (105, 125) are not aligned with the arrays in the intermediate plates (110, 120). Indeed, the arrays of apertures are arranged such that none of the holes in the surfaces that contact to each other will overlap. This concept is depicted in further detail in FIGS. 2 and 2A.

According to one embodiment, a composite interbody device 100 suitable for use in the lumbar region of the spine will have a width ranging from about 8 mm to about 20 mm, a height ranging from about 6 mm to about 16 mm, and a length ranging from about 25 mm to about 45 mm. According to another embodiment, a composite interbody device 100 for use in the cervical region of the spine will have a width ranging from about 12 mm to about 15 mm, a height ranging from about 6 mm to about 14 mm, and a length ranging from about 12 mm to about 15 mm. The interbody device 100 may also be provided with parallel or lordotic superior and inferior surfaces, depending upon the particularly anatomical needs of the patient. In addition, the interbody device 100 may be provided with concave or convex side walls to further suite the anatomical needs of the patient. The interbody device 100 may also be provided with a major aperture passing from the superior surface 106 of the first end plate 105, through the device 100, and to the inferior surface of the second end plate 125. The major aperture is used to promote bone through-growth in the device and can be loaded with appropriate materials (e.g., biologics, hydroxyapatite, etc.) to encourage through-grown of the bone to promote fusion of the adjacent vertebrae.

Figure 2:
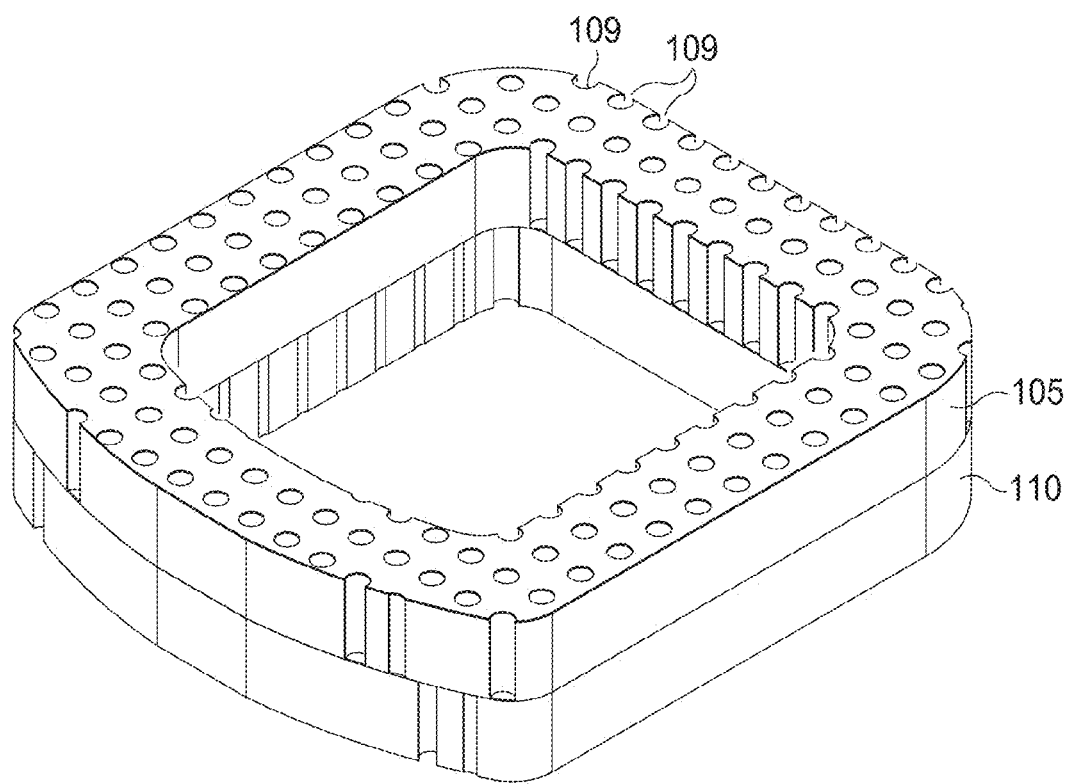
FIG. 2 is a perspective view of an exemplary embodiment of a metallic portion of a composite interbody device, according to one aspect of the invention.
Figure 2A:
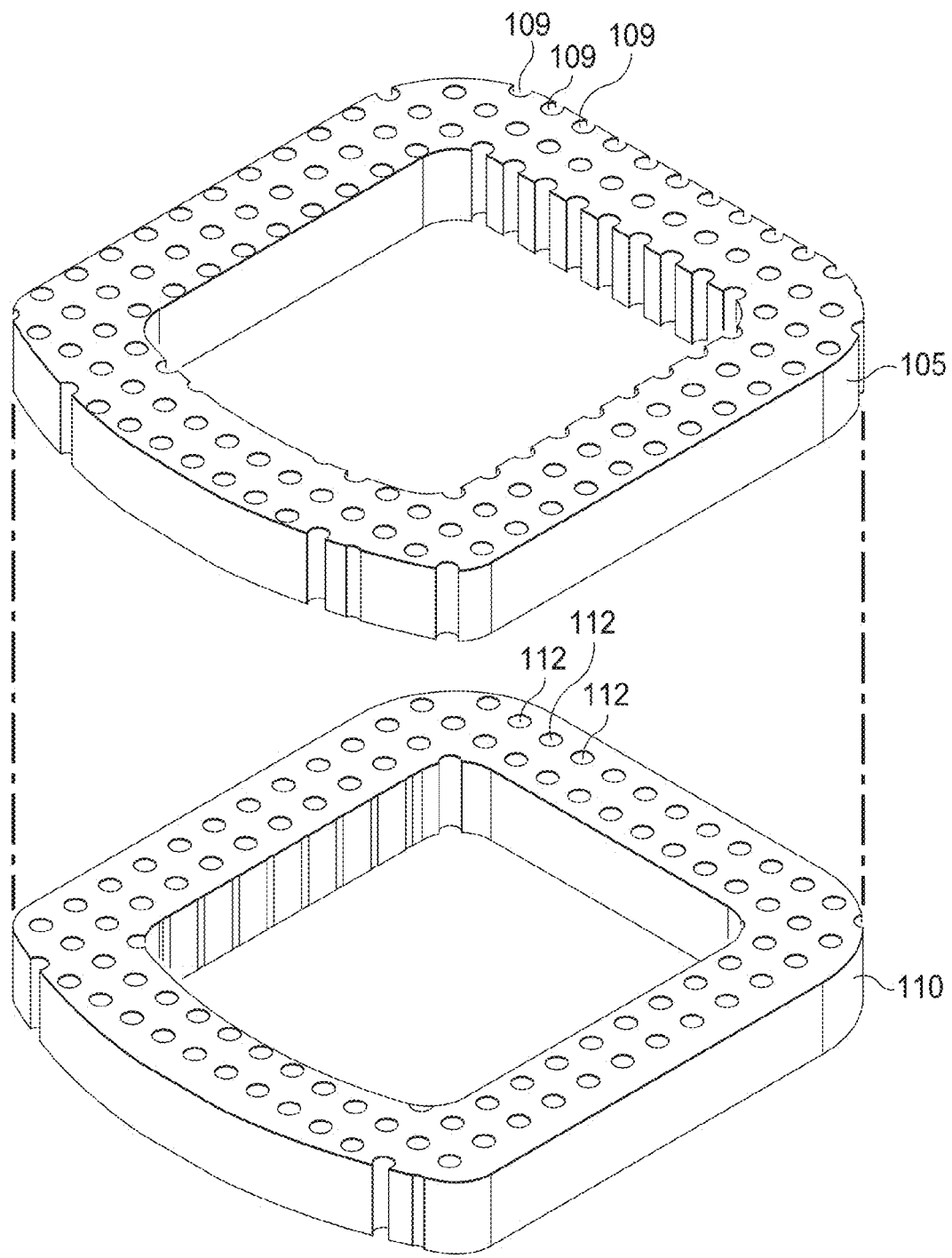
FIG. 2A is an exploded perspective view of an exemplary embodiment of a metallic portion of a composite interbody device, according to one aspect of the invention.

In FIG. 2, a first end plate 105 is depicted as being connected to a first intermediate plate 110. FIG. 2A is an exploded view of the first end plate 105 and the first intermediate plate 110. An array of apertures 109 in the first end plate is also depicted in FIGS. 2 and 2A. Also shown in FIG. 2A is an array of apertures 112 in the first intermediate plate 110. The non-alignment of the arrays of apertures 109 and 112 can be seen in FIG. 2A.

Figure 3:
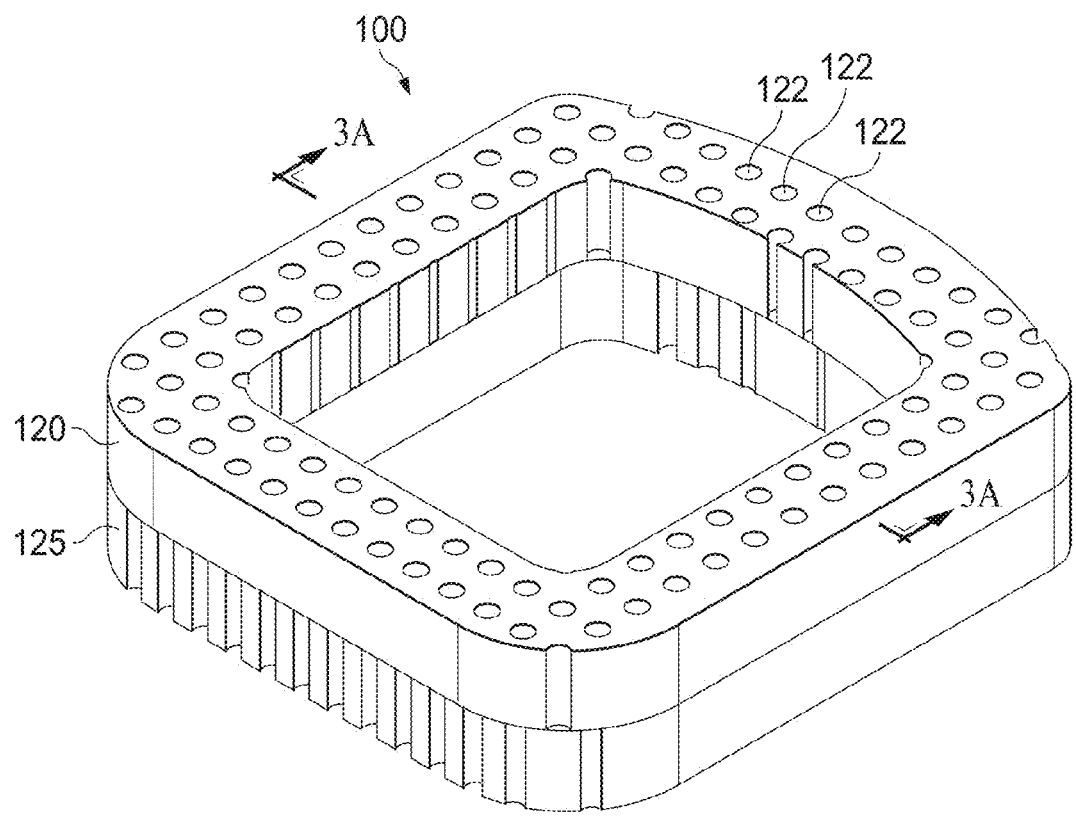
FIG. 3 is a perspective view of an exemplary embodiment of a metallic portion of a composite interbody device, according to one aspect of the invention.
Figure 3A:
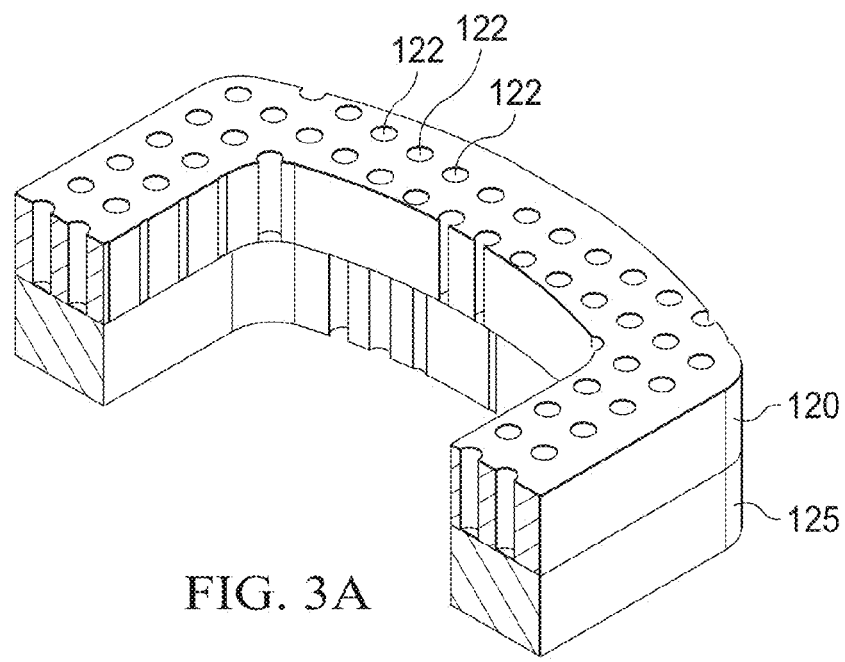
FIG. 3A is a cross-sectional perspective view of an exemplary embodiment of a metallic portion of a composite interbody device, according to one aspect of the invention.
Figure 3B:
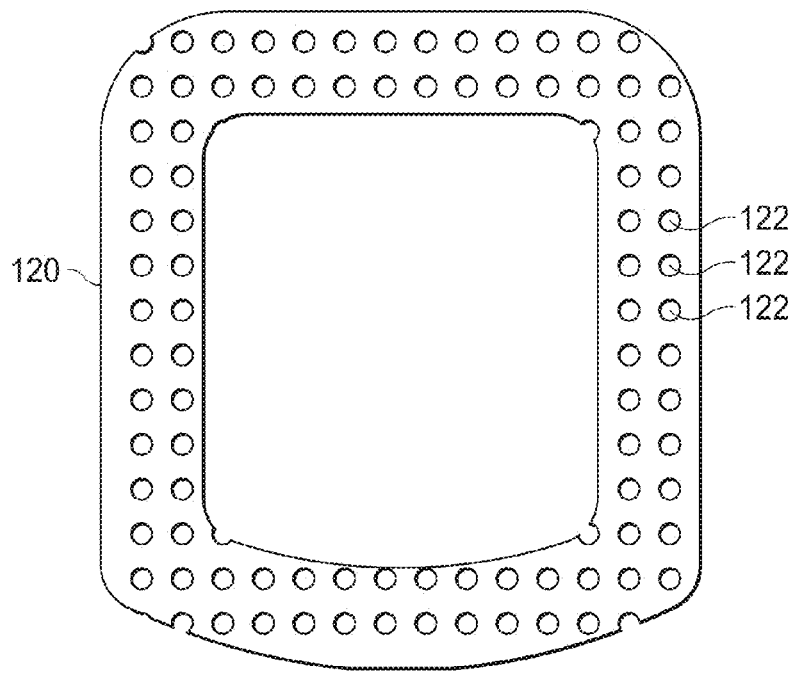
FIG. 3B is a top view of an exemplary embodiment of a metallic portion of a composite interbody device, according to one aspect of the invention.

Yet another view of the non-alignment of the arrays of apertures is depicted in FIGS. 3 and 3A. In FIG. 3, a second intermediate plate 120 is depicted as being connected to a second end plate 125. Much like the plates shown in FIGS. 2 and 2A, the array of apertures 122 in the second intermediate plate 120 are not aligned with the array of apertures in the second end plate 125. This non-alignment is apparent by examining the cross-section of the composite inter-body device 100 taken along axis A and depicted in FIG. 3A. In FIG. 3A, the cross-section passes through four apertures in the second intermediate plate 120, but does not pass through any of the apertures found in the second end plate 125. A top view of the second intermediate plate 120 and its corresponding array of apertures 122 is depicted in FIG. 3B.

Figure 4:
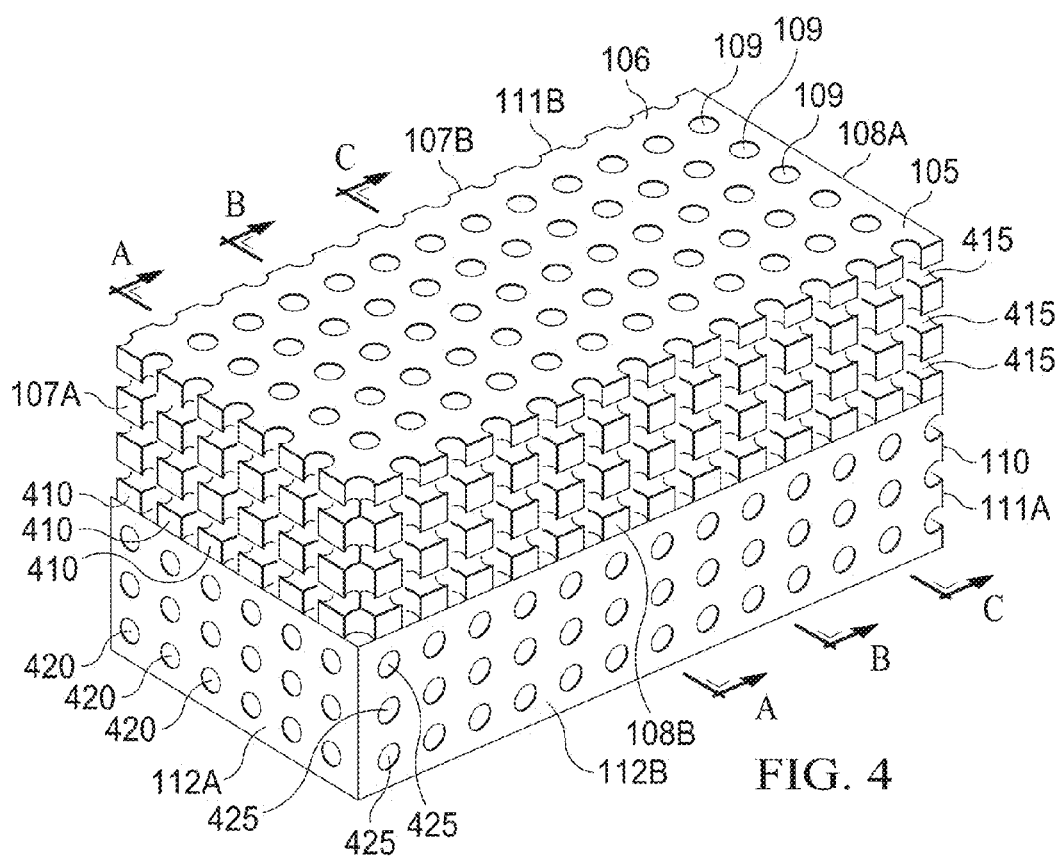
FIG. 4 is a perspective view of an exemplary embodiment of a metallic portion of a composite interbody device, according to one aspect of the invention.

According to another embodiment of the invention, the end plates (105, 125) and the intermediate plates (110, 120) may further comprise a second and third array of apertures. In the embodiments depicted in FIGS. 1, 2 and 3, the first array of apertures passes from the superior surface of the plate, through the plate, to the interior surface of the plate. In FIG. 4, a second array of apertures is depicted as passing from the interior side walls of the plates to the exterior side walls of the plates. In particular, as shown in FIG. 4, a first end plate 105 comprises a first array of apertures 109 that pass from the superior surface 106 to the interior surface (not shown) of the end plate 105. A second array of apertures 410 pass from an interior side wall 108A of the first end plate 105 to an exterior side wall 107A of the end plate 105. In addition, a third array of apertures 415 may be utilized that pass from another interior side wall 108B of the first end plate 105 to the other exterior side wall 107B of the end plate 105. This third array of apertures is marked in FIG. 4 with reference numbers 415. Also shown in FIG. 4 is a second and third array of apertures located in the first intermediate plate 110. The second array of apertures 420 in the first intermediate plate 110 pass from an interior side wall 112A to an exterior side wall 111A of the first intermediate plate 110. Similarly, a third array of apertures 425 pass from another interior side wall 112B to another exterior side wall 111B of the first intermediate plate 110. Preferably, the first, second and third array of apertures in each plate are orthogonal with respect to each other thereby forming an interconnected rectangular void of apertures in each plate.

Figure 4A:
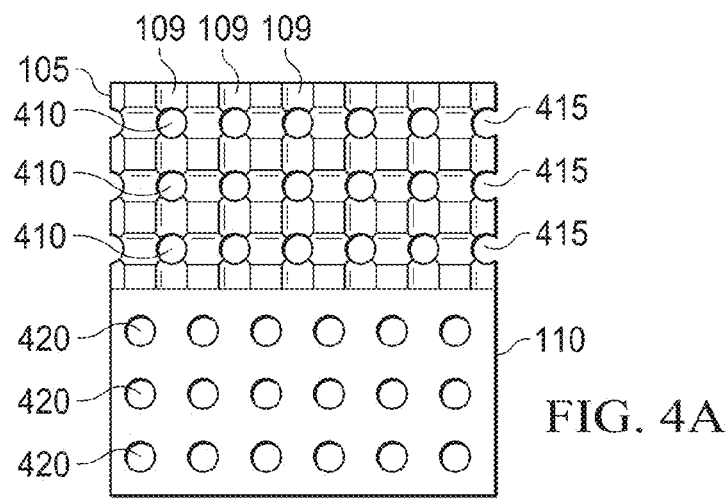
FIG. 4A is a cross-section view of an exemplary embodiment of a metallic portion of a composite interbody device, according to one aspect of the invention.

FIG. 4A is a cross-sectional view of the combination of the first end plate 105 with the first intermediate plate 110 taken along axis A. In FIG. 4A, the second array of apertures 410 are depicted in circular cross-section, while the first array of apertures 109 and the third array of apertures 415 are depicted in rectangular cross-section. This is due to the cross-section A being taken along the longitudinal axis of the first array of apertures 109 and the third array of apertures 415. In addition, due to the non-alignment of the arrays of apertures between the first end plate 105 and the first intermediate plate 110, only the second array of apertures 420 in the first intermediate plate 110 are depicted in circular cross-section. There is no overlap of the apertures between the first end plate 105 and the first intermediate plate 110.

Figure 4B:
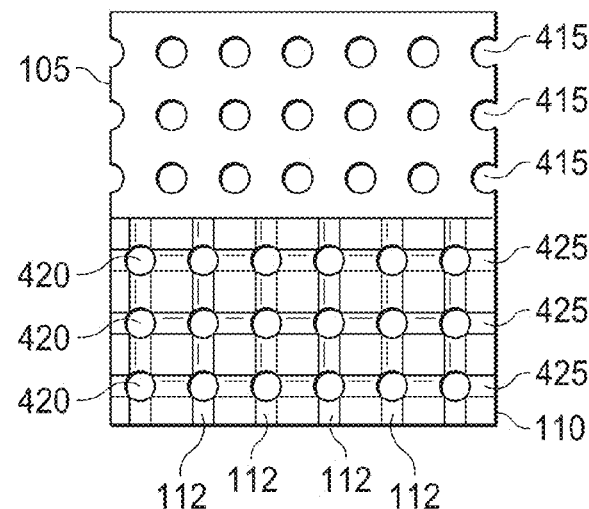
FIG. 4B is a perspective view of an exemplary embodiment of a metallic portion of a composite interbody device, according to one aspect of the invention.

FIG. 4B depicts a cross-section of the combination of the first end plate 105 and the first intermediate plate 110 taken along axis B of FIG. 4. In FIG. 4B, only the second array of apertures 415 is visible in the first end plate 105 since the cross-section axis B does not intersect with the first or third array of apertures in the first end plate 105. In contrast, all three arrays of apertures are visible in the first intermediate plate 110. The second array of apertures 420 is visible in circular cross-section, while the first array of apertures 112 and the third array of apertures 425 are depicted in rectangular cross-section. Again, this is due to the non-alignment of the arrays of apertures between the first end plate 105 and the first intermediate plate 110.

Figure 4C:
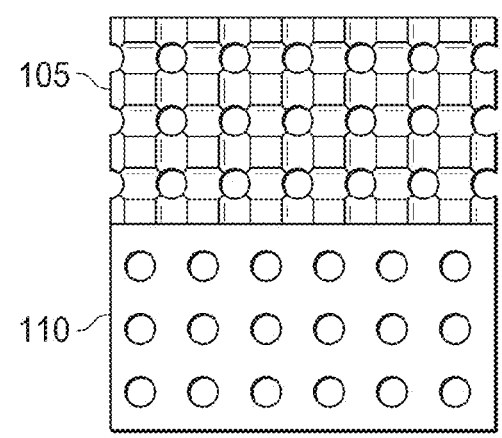
FIG. 4C is a perspective view of an exemplary embodiment of a metallic portion of a composite interbody device, according to one aspect of the invention.

FIG. 4C is a cross-sectional view of the combination of the first end plate 105 with the first intermediate plate 110 taken along axis C in FIG. 4. The arrangement of the arrays of apertures in the first end plate 105 and in the first intermediate plate 110 is identical to the arrangement shown in FIG. 4A, thus showing the repeating pattern of the arrays of apertures.

Figure 5A:
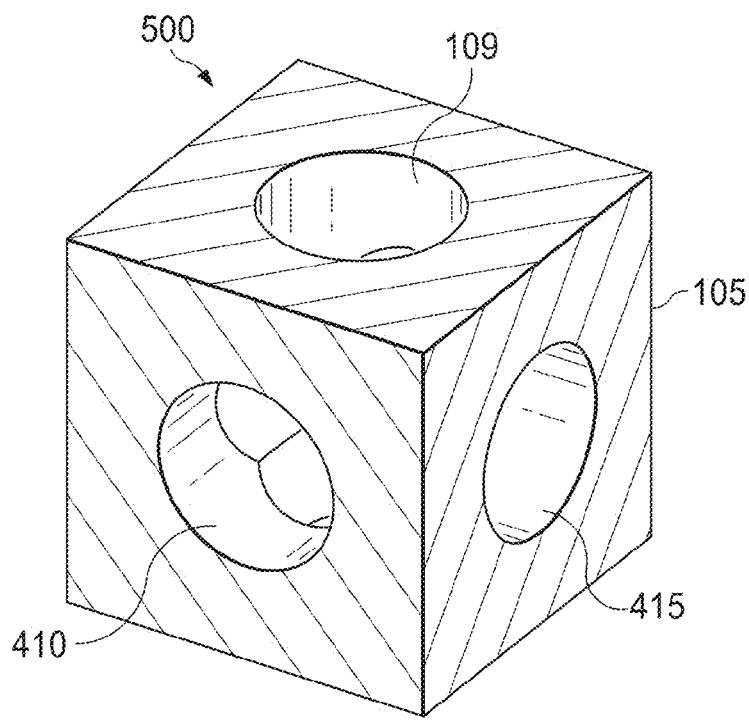
FIG. 5A is a three dimensional cross-section view of a portion of a metallic plate of a composite interbody device, according to one aspect of the invention.
Figure 5B:
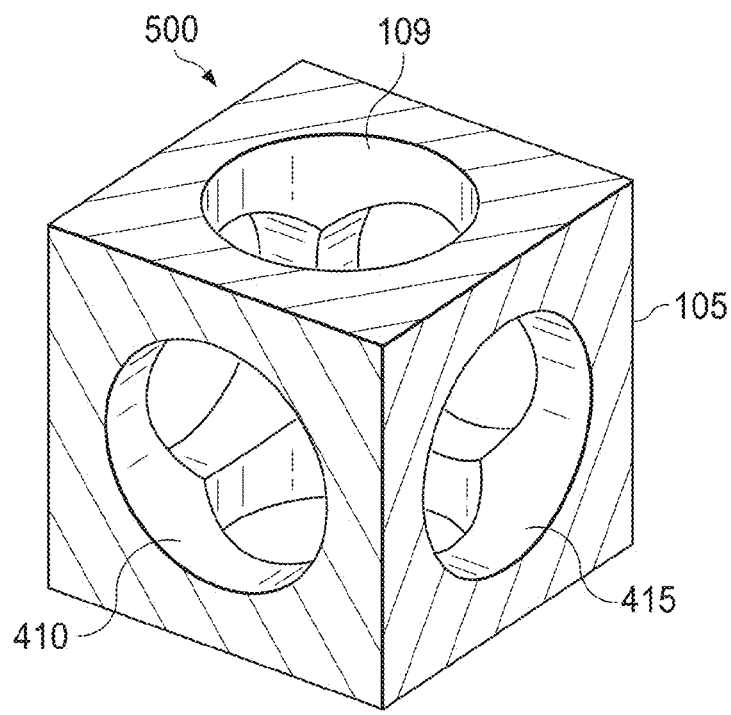
FIG. 5B is a three dimensional cross-section view of a portion of a metallic plate of a composite interbody device, according to one aspect of the invention.

A three-dimensional cross-section of the intersection of the apertures is depicted in FIGS. 5A and 5B. In FIG. 5A, a three-dimensional cross-section has been taken of the first end plate 105 showing the intersection of aperture 109 with aperture 410 and aperture 415. Depending upon the size of the aperture, a varying volume of material is removed from the interior of the end plate 105. In FIG. 5A, the size of apertures 109, 410, and 415 has been adjusted so that approximately 40% of the volume of the cubic cross-section 500 has been removed. In FIG. 5B, a similar cubic cross-section is depicted of a section of the first end plate 105. In FIG. 5B, apertures 109, 410, and 415 are larger than the apertures depicted in FIG. 5A. As a result, approximately 60% of the volume of the cubic cross-section 500 has been removed by the apertures.

According to one embodiment, the end plates 105 and 125 may utilize a first, second and third array of apertures that intersect with each other such that somewhere between about 40% to about 70% of the volume of the end plates (105, 125) are removed. Removal of this volume has two beneficial effects. First, it creates a frictional surface on the vertebrae-facing surfaces that discourage relative movement of the interbody device 100 with respect to the adjacent vertebrae. Second, the rectangular void created by the intersection of the arrays of apertures promotes bone on-growth, in-growth, and through-growth into the end plates (105, 125). According to one embodiment, the size of the apertures in the end plates can range from 0.25 to 0.5 millimeters.

According to another aspect, the intermediate plates 110 and 120 may also utilize first, second, and third arrays of apertures that intersect each other. The apertures in the intermediate plates (110, 120) may have smaller sizes such that the intermediate plates have only 30% to 60% of the volume of those plates removed by the arrays of apertures. The size of the apertures in the intermediate plates 110 and 120 can be in the range of 0.25 to 0.5 millimeters.

Figure 6:
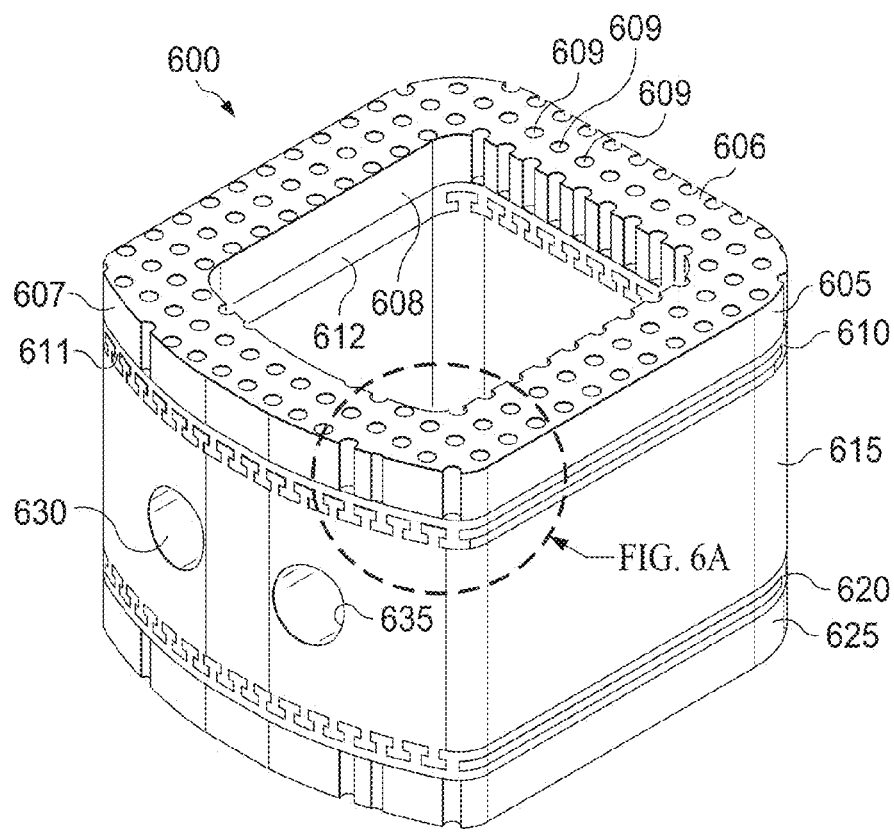
FIG. 6 is a perspective view of another exemplary embodiment of a composite interbody device.

An alternative embodiment of a composite interbody device 600 is depicted in FIG. 6. In FIG. 6, a first end plate 605 is comprised of a biocompatible metal, such as surgical stainless steel, titanium, or composites thereof. The first end plate 605 includes a superior surface 606, an inferior surface (not visible), an exterior side wall 607, and an interior side wall 608 wherein the interior and exterior side walls (607, 608) connect the superior surface 606 to the inferior surface. In FIG. 6, a first array of apertures 609 is depicted that pass from the superior surface of the end plate 606 to the inferior surface of the endplate. Much like the embodiments described in FIGS. 1-4, the first end plate 605 may also include second and third arrays of apertures that pass from the interior side walls of the end plate 608 to the exterior side walls of the end plate 607. As described previously, these arrays of apertures can intersect and form a three-dimensional network of openings in the first end plate 605 into which bone through-growth may occur.

Also depicted in FIG. 6 is a first intermediate plate 610 that includes a superior surface (not shown) that connects to the inferior surface of the first end plate 605. The first intermediate plate 610 may be comprised of a biocompatible metal, such as surgical stainless steel, titanium, or composites thereof. The first intermediate plate includes an exterior end wall 611 and an interior end wall 612 that connect the superior surface to the inferior surface. The inferior surface of the first intermediate plate 610 further includes an array of linear recesses 612 that pass from one exterior side wall 611 to another opposing exterior side wall 611. A magnified view of a representative example of these linear recesses 612 is depicted in FIG. 6A.

Figure 6A:
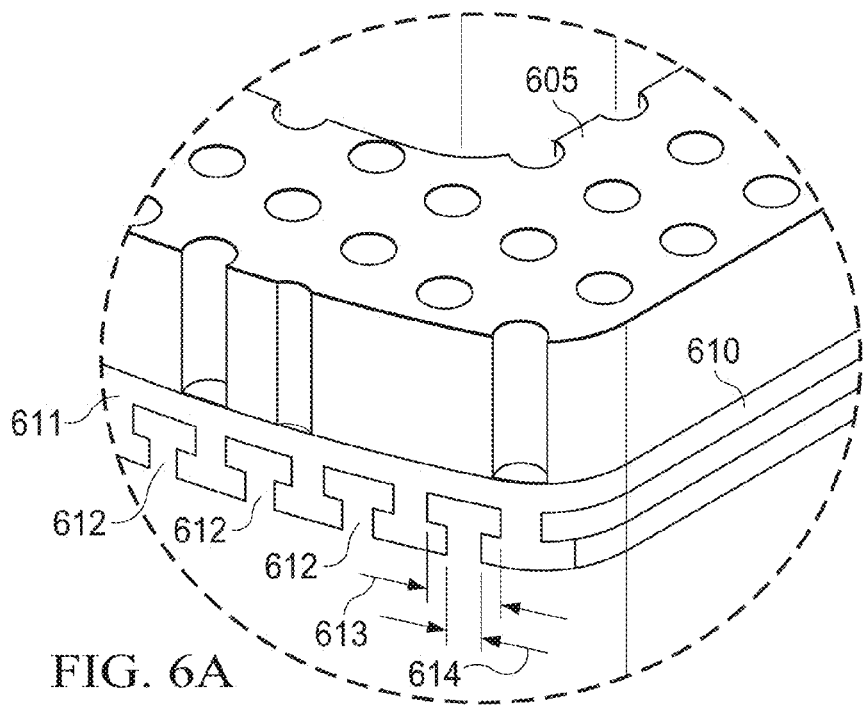
FIG. 6A is a close-up perspective view of an exemplary embodiment of a composite interbody device.

In FIG. 6A, each of the linear recesses has a T-shaped cross section in which the recess has a wider body portion 613 that is deeper inside the first intermediate plate 610 and a narrower neck portion 614 that is on the surface of the first intermediate plate 610. Although this disclosed embodiment uses a linear recess 612 with a T-shaped cross section, other shapes and forms of the linear recesses can be utilized. According to another embodiment, the inferior surface of the first intermediate layer 610 may further comprise a second array of linear recesses that are arranged orthogonally to the first array of linear recesses, thereby creating an array of protrusions from the inferior surface of the first intermediate layer. According to yet another embodiment, two arrays of orthogonal linear recesses with T-shaped cross-sections can be utilized.

Also depicted in FIGS. 6 and 6A is a central body 615 comprising a biocompatible polymer, such as PEEK, UHMWPE, or combinations thereof. The central body 615 includes a superior surface that connects to the inferior surface of first intermediate plate 610 and an inferior surface that connects to the superior surface of the second intermediate plate 620. The superior surface of the second intermediate plate 620 may utilize an array of linear recesses 612 in the same way that as the first intermediate plate 610. In addition, the inferior surface of the second intermediate plate 620 is connected to a second end plate 625 that may include a first, second, and third array of apertures that intersect and form a three-dimensional network of openings in the second plate 625 into which bone through-growth may occur.

Figure 7:
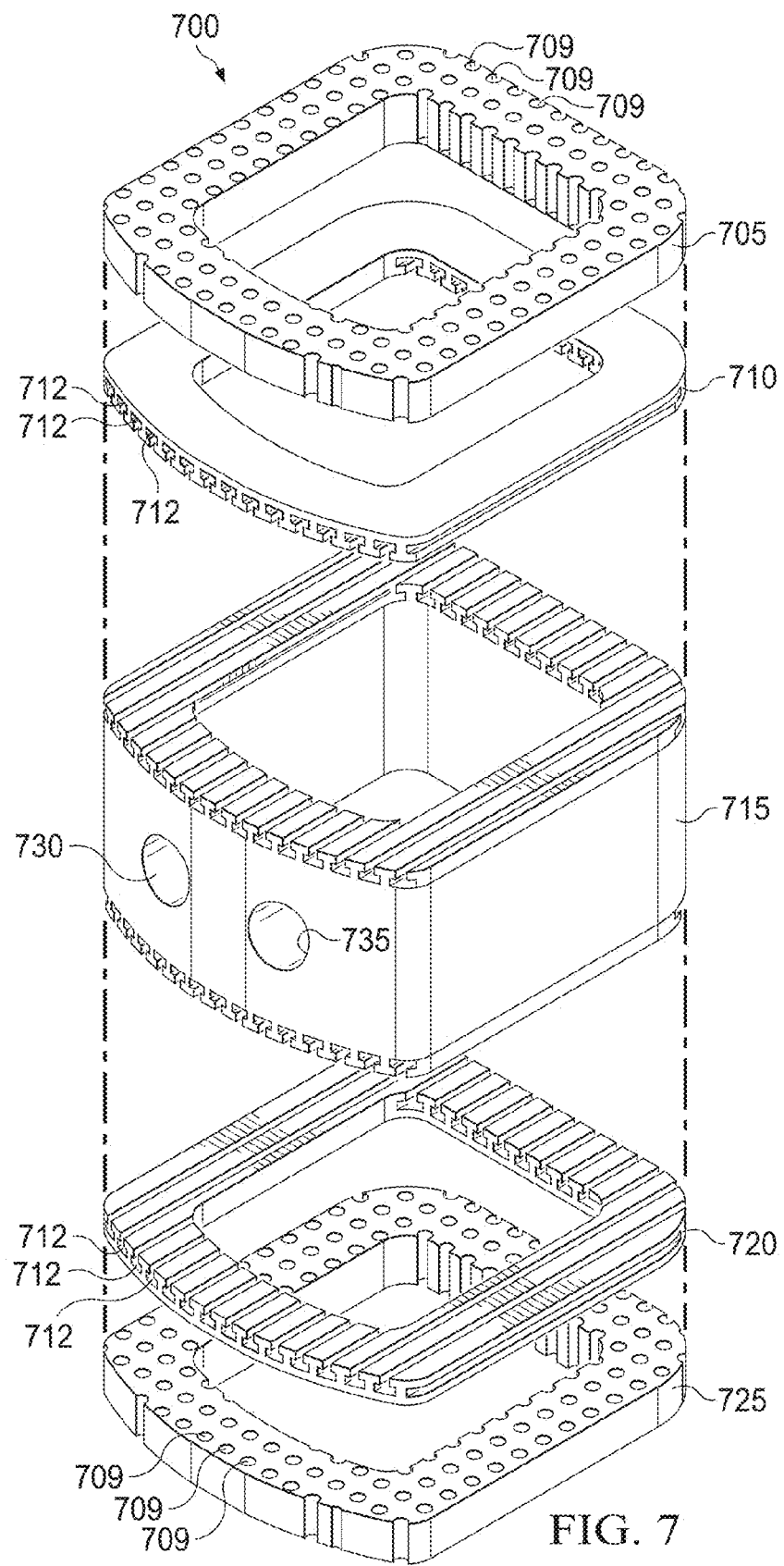
FIG. 7 is an exploded perspective view of another exemplary embodiment of a composite interbody device.

An exploded perspective view of the composite interbody device 700 depicted in FIG. 6 is depicted in FIG. 7. In FIG. 7, a first end plate 705, a first intermediate plate 710, a central body 715, a second intermediate plate 720, and a second end plate 725 are depicted. An array of linear recesses 712 with T-shaped cross sections are depicted in both intermediate plates (710, 720) and a first array of apertures 709 are depicted in both end plates (705, 725). As mentioned previously, second and third arrays of apertures can be added to the end plates (705, 725) to form three-dimensional networks of openings in the end plates (705, 725) to facilitate bone through-growth.

According to one embodiment, a composite interbody device can be fabricated according to the following process. End plates (105, 125) are formed from a biocompatible metal in a generally flat arrangement having a superior surface, an inferior surface, interior end walls that connect the superior surface to the inferior surface, and exterior end walls that connect the superior surface to the inferior surface. The thickness of the end plates may range from 0.5 mm to 1.5 mm, depending upon the anatomical placement of the implant and other surgical considerations. The end plates (105, 125) can be formed from a sheet of biocompatible metal, milled, or folded as needed to create the desired contours and shape. According to one embodiment, the biocompatible metal may include one or more arrays of apertures (109, 410, 415) prior to the fabrication of the end plates. According to another embodiment, the arrays of apertures (109, 410, 415) may be formed after the end plates have been fabricated. The intermediate plates (110, 120) can be fabricated using a similar process to the end plates (105, 125). However, care should be taken to ensure that the arrays of apertures in the intermediate plates (112, 420, 425) are offset from the arrays of apertures in the end plates so that none of the apertures of these two plates intersect with each other. The thickness of the intermediates plates (110, 120) may range from 0.25 mm to 0.8 mm, depending upon the anatomical placement of the implant and other surgical considerations. After the end plates (105, 125) and intermediate plates (110, 120) have been fabricated, the are connected to each other through metal bonding or any other appropriate joining process.

The central body 115 can be formed in a variety of ways. According to one embodiment, the central body 115, is milled from a solid piece of biocompatible polymer, such as PEEK or UHMWPE. After the central body 115 has been formed, it can be joined to the first and second end plates by heating the central body 115 to a flow temperature of the biocompatible polymer such that the polymer begins to penetrate the apertures or recesses in the intermediate plates (110, 120) to form a strong bond with those plates. The end plates (105, 125) may be compressed towards each other during this process to encourage the penetration of the biocompatible polymer into the apertures or recesses in the intermediate plates (110, 120).

According to another embodiment, the central body 115 is formed through an injection molding process. According to this process, the end plates are placed into a appropriate mold and a biocompatible polymer is injected into the mold such that the polymer begins to penetrate the apertures or recesses in the intermediate plates (110, 120) to form a strong bond with those plates. Once the biocompatible polymer has set, the composite interbody device may be removed.

According to another aspect, the interior side walls (e.g., 108, 112) of the composite interbody device 100 may be formed after the end plates (105, 125) and intermediate plates (110, 120) have been joined to the central body 115. A CNC machine or other milling device can remove an interior portion of the device 100, thereby leaving interior side walls in place.

According to yet another aspect, the screw holes (130, 135) can be formed by a milling process before or after the connection of the end plates (105, 110). The screw holes (130, 135) can also be formed in the injection molding process, by using a suitable mold.

Figure 8:
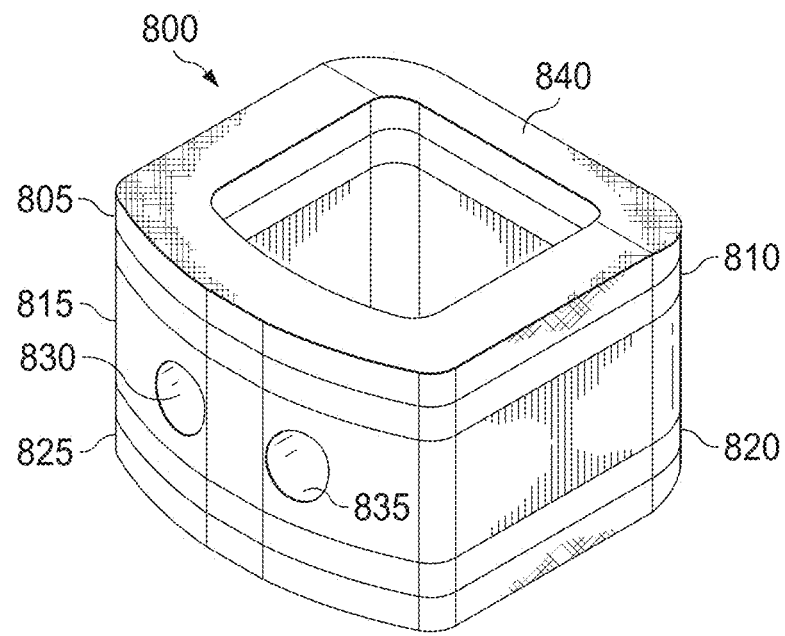
FIG. 8 is a perspective view of an exemplary embodiment of a composite interbody device suitable for use in the cervical region of the spine.

A exemplary embodiment of a composite interbody device suitable for insertion between cervical vertebrae is depicted in FIG. 8. In FIG. 8, a cervical composite interbody device 800 is depicted as comprising a first end plate 805, a first intermediate plate 810, a central body 815, a second intermediate plate 820, a second end plate 825, a first hole 830, and a second hole 835. As described previously, the end plates (805, 825) and intermediate plates (810, 820) are comprised of biocompatible metal and may include the arrays of apertures and linear recesses to facilitate bone through-growth and bonding to the central body. The cervical composite interbody device 800 may further include a bullet-shaped face 840 that will facilitate the insertion of the device between two adjacent cervical vertebrae.

Figure 9:
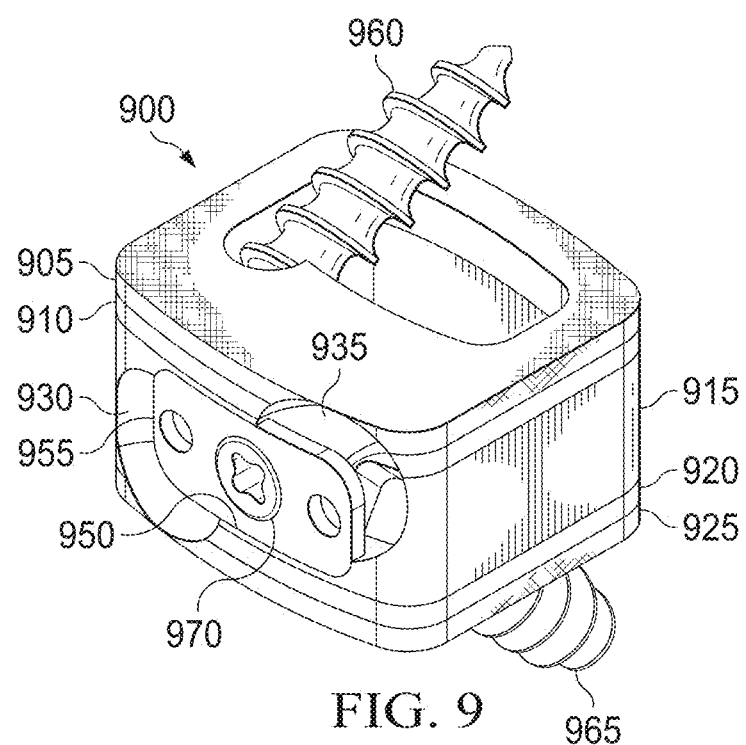
FIG. 9 is a perspective view of an exemplary embodiment of a composite interbody device with bone screws into adjacent vertebrae.

Another exemplary embodiment of a composite interbody device suitable for insertion between cervical vertebrae is depicted in FIG. 9. In FIG. 9, a cervical composite interbody device 900 is depicted as comprising a first end plate 905, a first intermediate plate 910, a central body 915, a second intermediate plate 920, a second end plate 925, a first angled screw hole 930, and a second angled screw hole 935. As described previously, the end plates (905, 925) and intermediate plates (910, 920) are comprised of biocompatible metal and may include the arrays of apertures and linear recesses to facilitate bone through-growth and bonding to the central body 915. The first angled screw hole 930 is oriented such that it intersects with the superior surface of the first end plate 905 and the second angled screw hole 935 is oriented such that it intersects with the inferior surface of the second end plate 925. First and second bone screws can be inserted into screw holes 930 and 935 to affix the interbody device 900 the adjacent vertebral bodies. The cervical composite interbody device 900 may further include a receptacle 950 for receiving a back-out plate 955 that is adjacent to angled screw holes 930 and 935. By inserting a back-out plate 955 and locking it into place with a locking screw, the bone screws 960 and 965 will be inhibited from backing out of the upper and lower vertebral bodies.

Figure 10:
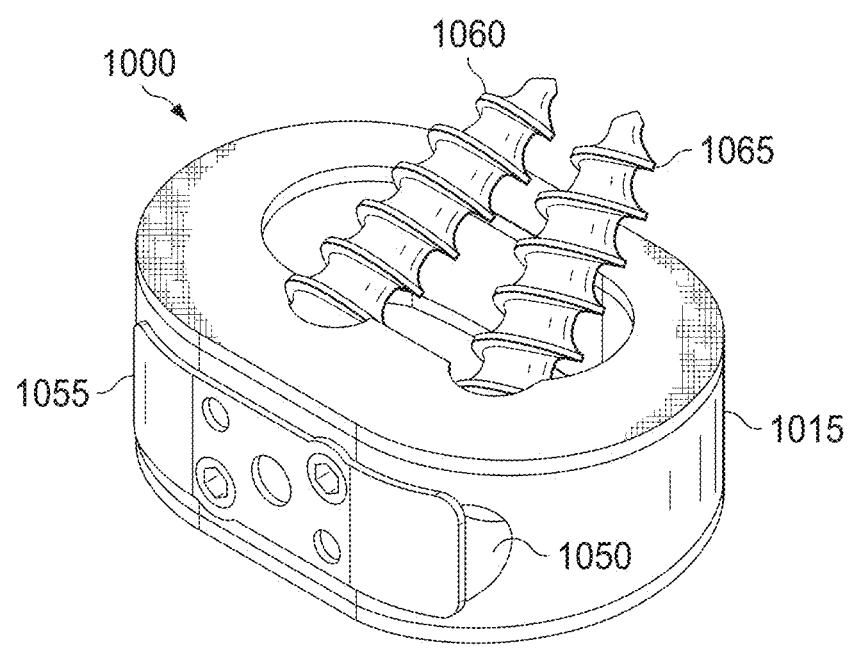
FIG. 10 is a perspective view of another exemplary embodiment of a composite interbody device with bone screws into adjacent vertebrae.

FIG. 10 is an embodiment of a composite interbody device 1000 suitable for insertion between adjacent lumbar vertebrae. In FIG. 10, the end plates and intermediate plates are comprised of biocompatible metal and may include the arrays of apertures and linear recesses to facilitate bone through-growth and bonding to the central body 1015. Angled screw holes are utilized, but both bone screws 1060, 1065 are drilled into one adjacent lumber vertebrae. The lumbar composite interbody device 1000 may further include a receptacle 1050 for receiving a back-out plate 1055 that is adjacent to the angled screw holes. By inserting a back-out plate 1055 and locking it into place with one or more locking screws, the bone screws 1060 and 1065 will be inhibited from backing out of the lumbar vertebral body.

Figure 11:
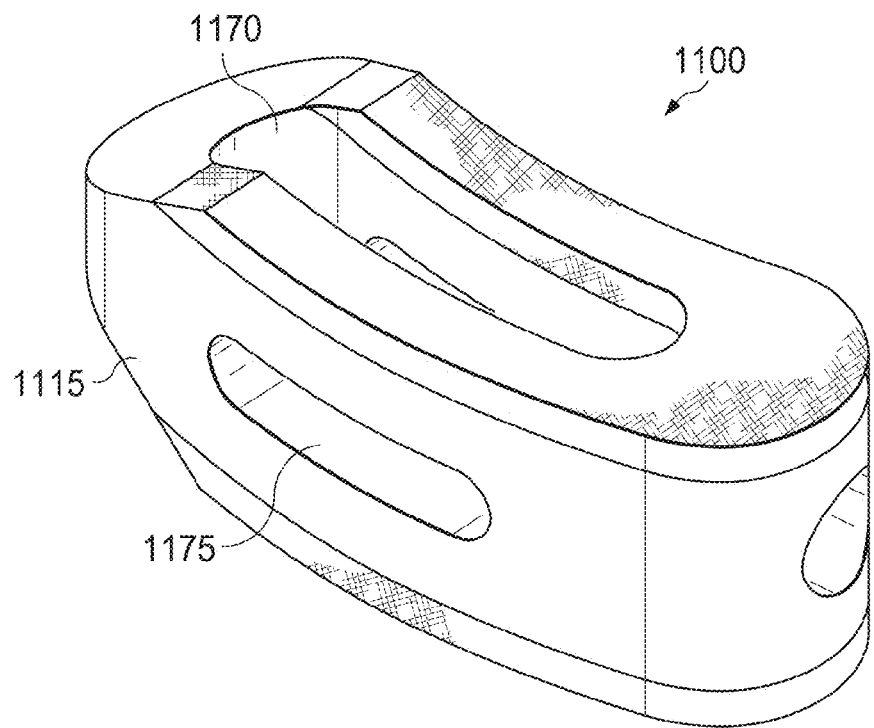
FIG. 11 is a perspective view of an exemplary embodiment of a composite interbody device in the shape of a TLIF or PLIF cage.

FIG. 11 depicts yet another alternative embodiment of a composite interbody device 1100 that may act as a TLIF or PLIF cage. In FIG. 11, the end plates and intermediate plates are comprised of biocompatible metal and may include the arrays of apertures and linear recesses to facilitate bone through-growth and bonding to the central body 1115, as described previously. In addition to a major aperture 1170 passing through the device 1100 that forms the interior end walls, the embodiment depicted in FIG. 11 includes one or more lateral apertures in the central body. These lateral apertures help to facilitate the bone in-growth and through-growth process into the device 1100.

Figure 12:
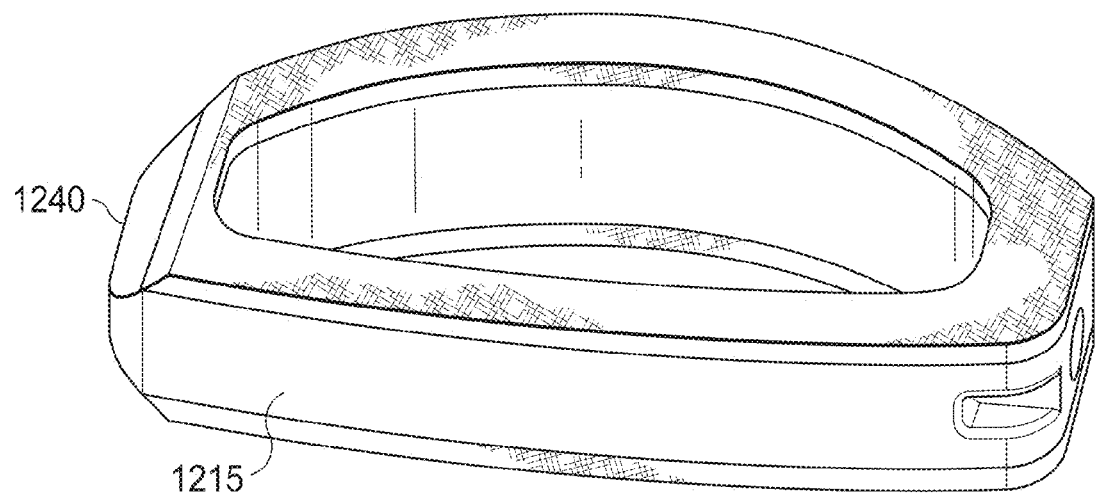
FIG. 12 is a perspective view of an exemplary embodiment of a composite interbody device in the shape of a lateral cage.

FIG. 12 depicts another alternative embodiment of a composite interbody device 1200 that may act as a lateral cage. In FIG. 12, the end plates and intermediate plates are comprised of biocompatible metal and may include the arrays of apertures and linear recesses to facilitate bone through-growth and bonding to the central body 1215, as described previously. The lateral composite interbody device 1200 may further include a bullet-shaped face 1240 that will facilitate the insertion of the device between two adjacent vertebrae from a lateral approach.

Figure 13:
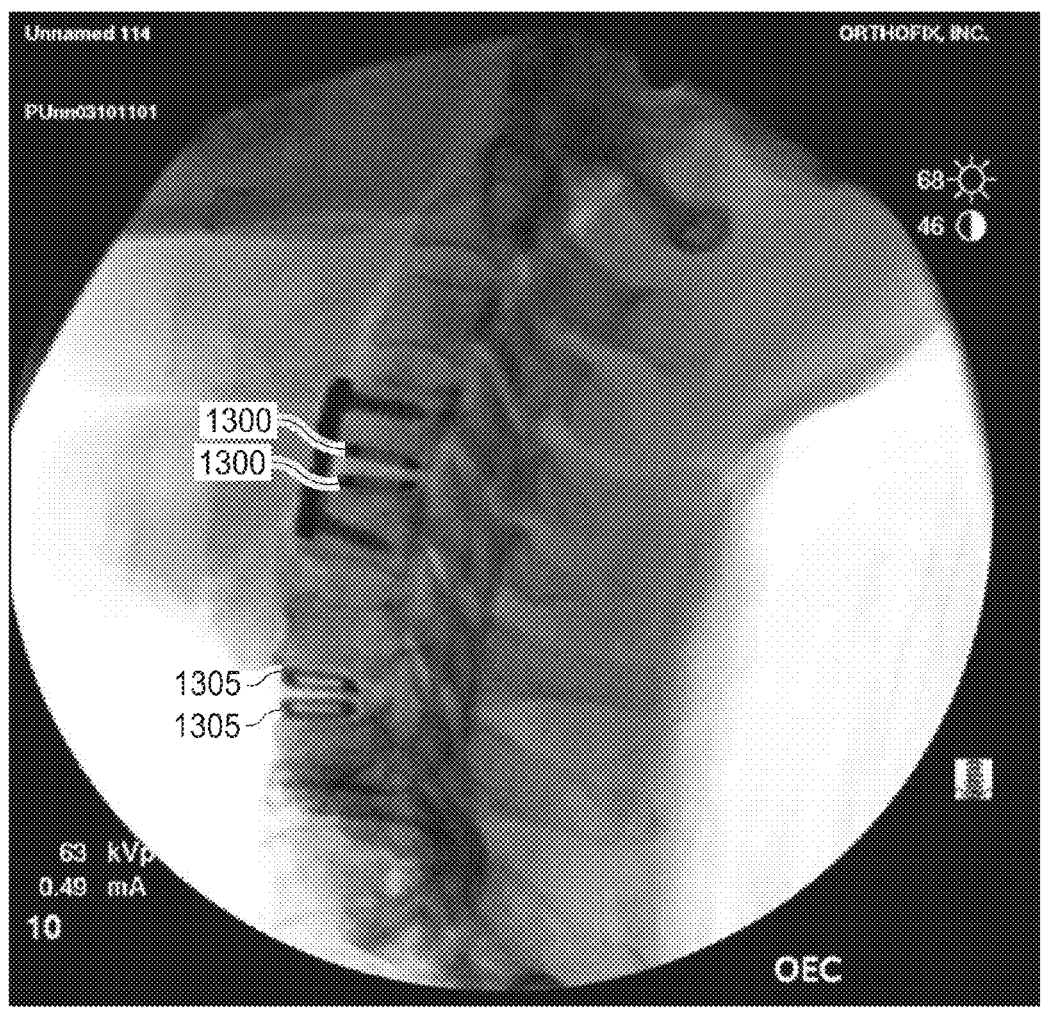
FIG. 13 is an exemplary radiograph of a composite interbody device after insertion between two adjacent vertebrae.

FIG. 13 is an exemplary radiograph of a patient's spine in which two composite interbody devices have been between adjacent vertebrae. In FIG. 13, a first interbody device 1300 can be seen between two adjacent vertebral bodies. Another interbody device 1305 is also depicted in FIG. 13. Since the central body 115 of the interbody devices (1300, 1305) is radiolucent, only the end plates and intermediate plates are visible in the radiograph. Accordingly, the placement of the interbody devices (1300, 1305) in the spine can be more readily monitored and the amount of bone on-growth, in-growth, and through-growth can also be readily monitored.

Figure 14A:
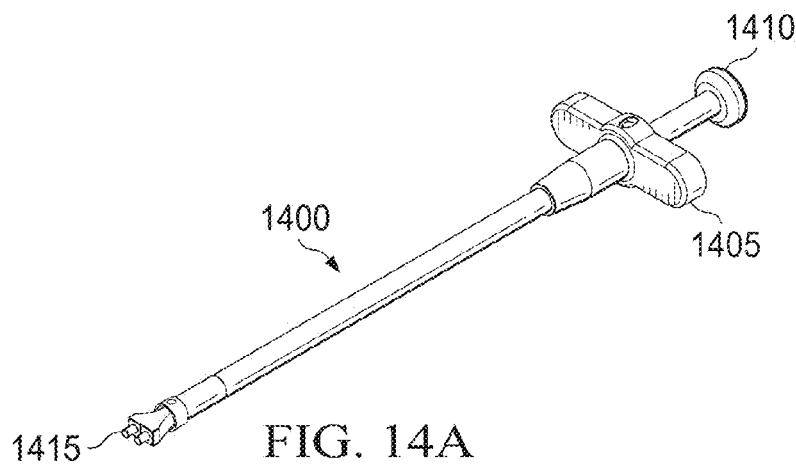
FIG. 14A is a perspective view of an exemplary embodiment of an installation tool for composite interbody device.
Figure 14B:
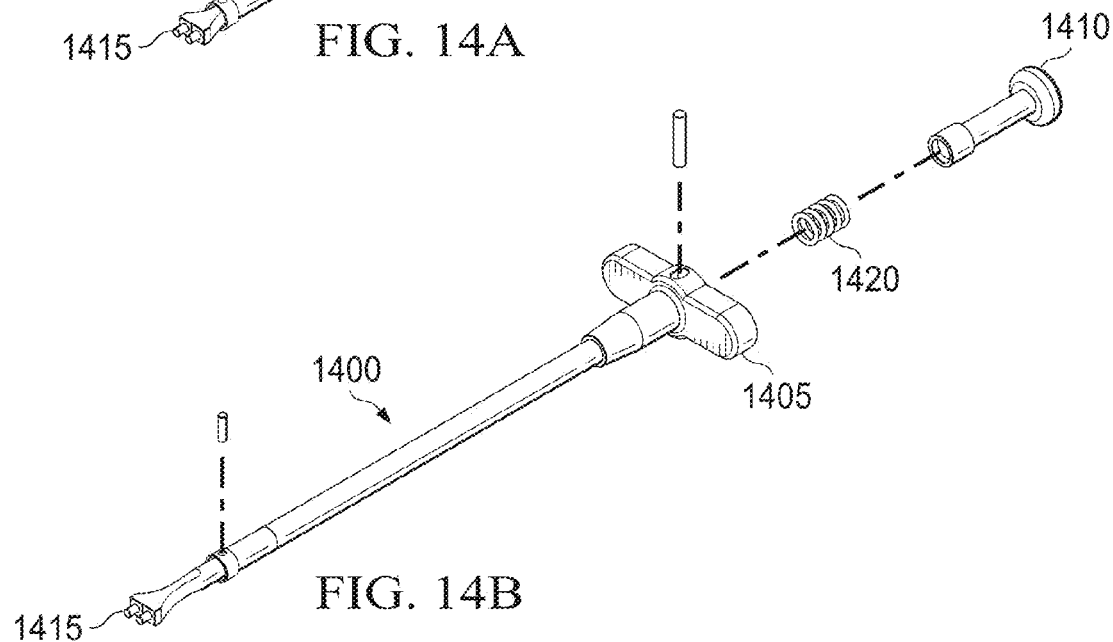
FIG. 14B is an exploded perspective view of an exemplary embodiment of an installation tool with a composite interbody device attached thereto.
Figure 14C:
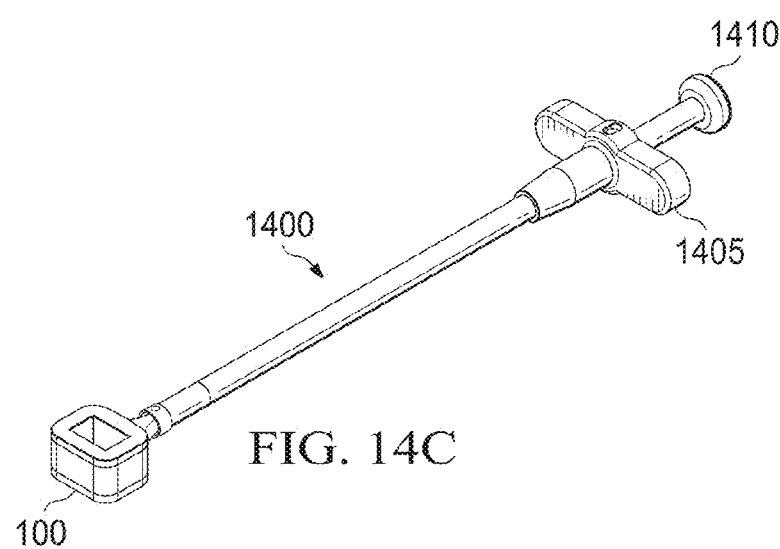
FIG. 14C is a perspective view of an exemplary embodiment of an installation tool for composite interbody device.

FIGS. 14A-14C depict an implantation tool 1400 that may be used to insert a interbody device 100 into the space between two adjacent vertebrae. As shown in FIGS. 14A-14C, the tool comprises a first handle 1405, a second handle 1410, a pair of lockable members 1415, and a spring 1420. The pair of lockable members 1415 may include prongs that face towards each other. To connect the implantation tool 1400 to the interbody device, the second handle 1410 is pressed towards the first handle 1405, thereby pressing against spring 1420 and pushing the pair of lockable members outwards from the distal end of the tool sheath. As the lockable members 1415 are pushed out of the sheath, the separate from each other, thus providing room for them to be inserted into the holes (130, 135) formed in an exterior side wall 116 of the central body 115. Once the lockable members 1415 inserted into the interbody device 100, the second handle can be released, thus causing the lockable members to retract within the sheath, thereby forming a releasable attachment to the composite interbody device 100 at end of the tool 1400. Once the interbody device 100 has been inserted between two adjacent vertebrae, the lockable members 1415 can be disengaged from the holes (130, 135) by pressing the second handle 1410 towards the first handle 1405 until the lockable members can be freely disengaged from the interbody device 100 while leaving the interbody device 100 in place.

Figure 15A:
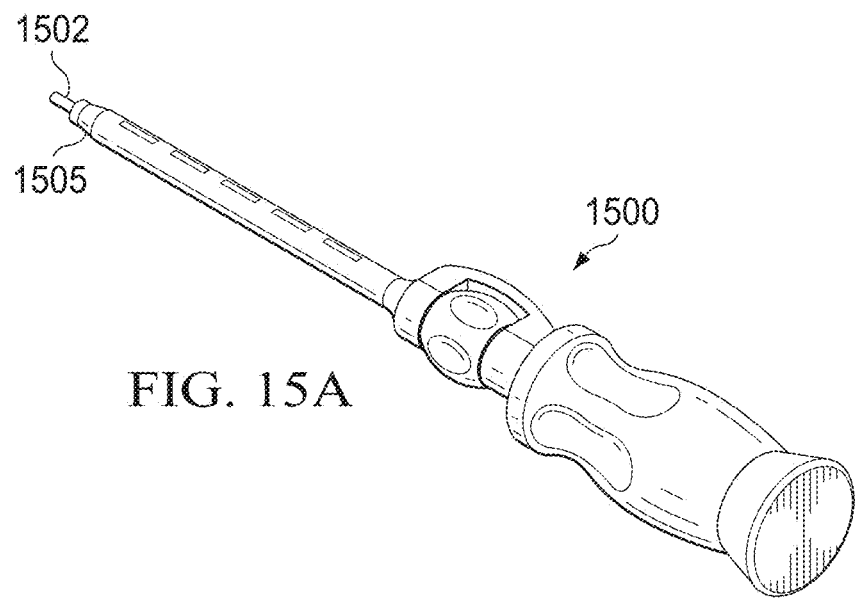
FIG. 15A is a perspective view of an exemplary embodiment of a locking device suitable for use with a composite interbody device.
Figure 15B:
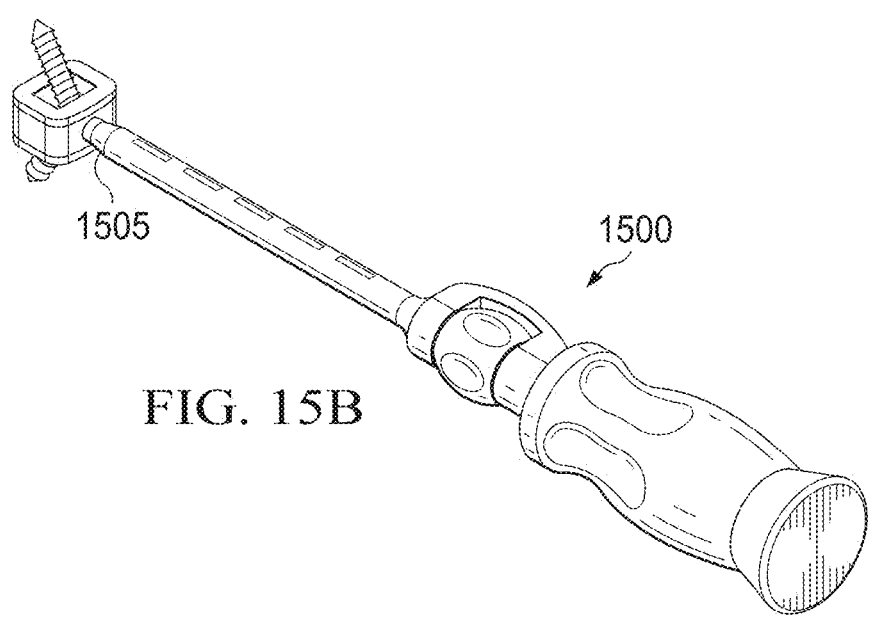
FIG. 15B is a perspective view of an exemplary embodiment of a locking device suitable for use with a composite interbody device.

FIGS. 15A and 15B depict an driving tool 1500 that may be used to lock a back-out plate (e.g., 955, 1055) onto the exterior side wall 116 of a interbody device 100. Typically, this procedure is performed after one or more bone screws has been used to attach the interbody device 100 to the adjacent vertebrae, as depicted in FIGS. 9 and 10. Once the bone screws have been set, a back-out plate (955, 1055) is put into place and a locking screw 1502 is releasably attached to a distal end 1505 of the driving tool 1500. The driving tool 1500 is then used to drive the locking screw 1502 through the back-out plate (955, 1055) into the central body 115, thus locking the back-out plate (955, 1055) against the interbody device 100. Once the back-out plate (955, 1055) has been locked to the interbody device, the locking screw 1502 can be released from the distal end 1505 of the driving tool 1500 and the driving tool can be removed from the intervertebral space.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A composite interbody device adapted for insertion between two adjacent vertebrae, the interbody device comprising:
 a first end plate comprising a biocompatible metal and having a superior surface adapted to contact an upper vertebral body, an inferior surface, an exterior side wall connecting the superior surface to the inferior surface, and an interior side wall connecting the superior surface to the inferior surface, the first end plate further comprising a first array of apertures passing from the superior surface to the inferior surface, at least one aperture of the first array of apertures passing from the superior surface through the first end plate to the inferior surface along a longitudinal axis oriented perpendicular to the superior surface of the first end plate;
 a first intermediate plate comprising a biocompatible metal and having a superior surface adapted to contact the inferior surface of the first end plate, an inferior surface, an exterior side wall connecting the superior surface to the inferior surface, and an interior side wall connecting the superior surface to the inferior surface, the first intermediate plate further comprising a first array of apertures passing from the superior surface to the inferior surface;
 a central body comprising a biocompatible polymer and having a superior surface adapted to contact the inferior surface of the first intermediate plate, an inferior surface, an exterior side wall connecting the superior surface to the inferior surface, and an interior side wall connecting the superior surface to the inferior surface;

a second intermediate plate comprising a biocompatible metal and having a superior surface adapted to contact the inferior surface of the central body, an inferior surface, an exterior side wall connecting the superior surface to the inferior surface, and an interior side wall connecting the superior surface to the inferior surface, the second intermediate plate further comprising a first array of apertures passing from the superior surface to the inferior surface;

a second end plate comprising a biocompatible metal and having a superior surface adapted to contact the inferior surface of the second intermediate plate, an inferior surface adapted to contact a lower vertebral body, an exterior side wall connecting the superior surface to the inferior surface, and an interior side wall connecting the superior surface to the inferior surface, the second end plate further comprising a first array of apertures passing from the superior surface to the inferior surface;

wherein the first array of apertures at the inferior surface of the first end plate do not overlap the first array of apertures at the superior surface of the first intermediate plate such that the biocompatible polymer of the central body is prevented from penetrating through the first intermediate plate into the first end plate when the inferior surface of the first end plate contacts the superior surface of the first intermediate plate;

wherein the first array of apertures at the inferior surface of the second intermediate plate do not overlap the first array of apertures at the superior surface of the second end plate when the inferior surface of the second intermediate plate contacts the superior surface of the second end plate.

2. A composite interbody device according to claim 1, wherein the first end plate further comprises a second array of apertures passing from the exterior side wall to the interior side wall and a third array of apertures passing from another exterior side wall to another interior side wall;

wherein the second end plate further comprises a second array of apertures passing from the exterior side wall to the interior side wall and a third array of apertures passing from another exterior side wall to another interior side wall;

wherein the first intermediate plate further comprises a second array of apertures passing from the exterior side wall to the interior side wall and a third array of apertures passing from another exterior side wall to another interior side wall; and wherein the second intermediate plate further comprises a second array of apertures passing from the exterior side wall to the interior side wall and a third array of apertures passing from another exterior side wall to another interior side wall.

3. A composite interbody device according to claim 2, wherein each of the second and third arrays of apertures in each of the first end plate, the first intermediate plate, the second end plate, and the second intermediate plate intersect the first arrays of apertures in the first end plate, first intermediate plate, the second end plate, and the second intermediate plate, respectively.

4. A composite interbody device according to claim 3, wherein the first, second, and third arrays of apertures in each of the first end plate, the first intermediate plate, the second end plate, and the second intermediate plate are substantially orthogonal to each other.

5. A composite interbody device according to claim 3, wherein the intersection of the first, second, and third arrays of apertures in each of the first end plate, the first intermediate plate, the second intermediate plate, and the second end plate creates an interconnected void of at least 40% of the volume of the first end plate, first intermediate plate, second intermediate plate, and second end plate, respectively.

6. A composite interbody device according to claim 3, wherein the intersection of the first, second, and third arrays of apertures in the first and second end plates creates an interconnected void in the range of about 40% to about 70% of the volume of the first and second end plates, respectively.

7. A composite interbody device according to claim 6, wherein the intersection of the first, second and third arrays of apertures in the first and second intermediate plates creates an interconnected void in the range of about 30% to about 60% of the volume of the first and second intermediate plates, respectively.

8. A composite interbody device according to claim 1, wherein the interior side walls of the first end plate, the first intermediate plate, the central body, the second intermediate plate, and the second end plate form a major aperture passing through interbody device from the superior surface of the first end plate to the inferior surface of the second plate.

9. A composite interbody device according to claim 1, wherein the central body further comprises:
a first screw hole passing from the exterior side wall of the central body to the interior side wall of the central body and towards one of the end plates, wherein the first screw hole is operable to receive a bone screw that connects to one of the vertebral bodies; and
a second screw hole passing from the exterior side wall of the central body to the interior side wall of the central body and towards one of the end plates, wherein the second screw hole is operable to receive a bone screw that connects to one of the vertebral bodies.

10. A composite interbody device according to claim 9, wherein the first screw hole intersects the superior surface of the first end plate and the second screw hole intersects an inferior surface of the second end plate.

11. A composite interbody device according to claim 9, wherein the central body further comprises a receptacle for receiving a back-out plate that is adjacent to the first and second screw holes, and wherein the back-out plate inhibits the bone screws from backing out of the upper and lower vertebral bodies.

12. A composite interbody device according to claim 1, wherein the exterior side wall of the central body further comprises a tool receptacle for receiving a insertion tool that can be releasably connected to the interbody device during the implantation of the device between adjacent vertebrae.

13. A composite interbody device according to claim 1, wherein the interbody device is shaped to be inserted between adjacent vertebrae in the cervical region of the spine.

14. A composite interbody device according to claim 1, wherein the interbody device is shaped to be inserted between adjacent vertebrae in the lumbar region of the spine.

15. A composite interbody device according to claim 1, wherein the central body comprises a radiolucent material for monitoring an amount of bone on-growth and through-growth.

16. A composite interbody device according to claim 1, wherein the superior surface of the first end plate further comprises spikes or ridges for restricting relative movement of the composite interbody device with respect to the upper vertebral body.

17. A composite interbody device according to claim 1, wherein, in the first and second intermediate plates, at least one of the first array of apertures each pass from the superior surface through the intermediate plate to the inferior surface.

18. A composite interbody device according to claim 1, wherein, in the second end plate, at least one of the first array of apertures each pass from the superior surface through the second end plate to the inferior surface.

19. A composite interbody device adapted for insertion between two adjacent vertebrae, the interbody device comprising:
a first end plate comprising a biocompatible metal and having a superior surface adapted to contact an upper vertebral body, an inferior surface, an exterior side wall connecting the superior surface to the inferior surface, and an interior side wall connecting the superior surface to the inferior surface, the first end plate further comprising a first array of apertures passing from the superior surface to the inferior surface, at least one aperture of the first array of apertures passing from the superior surface through the first end plate to the inferior surface along a longitudinal axis oriented perpendicular to the superior surface of the first end plate;
a first intermediate plate comprising a biocompatible metal and having a superior surface adapted to contact the inferior surface of the first end plate, an inferior surface, an exterior side wall connecting the superior surface to the inferior surface, and an interior side wall connecting the superior surface to the inferior surface, wherein the inferior surface of the first intermediate plate further comprises a first array of linear recesses, at least one linear recess of the first array of linear recesses passing from an exterior side wall to an opposing exterior side wall along a transverse axis oriented perpendicular to the exterior side wall of the first intermediate plate;
a central body comprising a biocompatible polymer and having a superior surface adapted to contact the inferior surface of the first intermediate plate, an inferior surface, an exterior side wall connecting the superior surface to the inferior surface, and an interior side wall connecting the superior surface to the inferior surface;
a second intermediate plate comprising a biocompatible metal and having a superior surface adapted to contact the inferior surface of the central body, an inferior surface, an exterior side wall connecting the superior surface to the inferior surface, and an interior side wall connecting the superior surface to the inferior surface, the second intermediate plate further comprising a first array of linear recesses passing from an exterior side wall to an opposing exterior side wall;
a second end plate comprising a biocompatible metal and having a superior surface adapted to contact the inferior surface of the second intermediate plate, an inferior surface adapted to contact a lower vertebral body, an exterior side wall connecting the superior surface to the inferior surface, and an interior side wall connecting the superior surface to the inferior surface, the second end plate further comprising a first array of apertures passing from the superior surface to the inferior surface.

20. A composite interbody device according to claim 19, wherein one or more of the linear recesses of both the first and second intermediate plates has a T-shaped cross section.

21. A composite interbody device according to claim 19, wherein the first end plate further comprises a second array of apertures passing from the exterior side wall to the interior side wall and a third array of apertures passing from another exterior side wall to another interior side wall; and
wherein the second end plate further comprises a second array of apertures passing from the exterior side wall to the interior side wall and a third array of apertures passing from another exterior side wall to another interior side wall.

22. A composite interbody device according to claim 21, wherein each of the second and third arrays of apertures in the first end plate and the second end plate intersect the first arrays of apertures of the first end plate and the second end plate, respectively.

23. A composite interbody device according to claim 22, wherein each of the first, second, and third arrays of apertures in each of the first end plate and the second end plate is substantially orthogonal to the other arrays of apertures.

24. A composite interbody device according to claim 22, wherein the intersection of the first, second, and third arrays of apertures in the first and second end plates creates an interconnected void of at least 40% of the volume of the first and second end plates, respectively.

25. A composite interbody device according to claim 22, wherein the intersection of the first, second and third arrays of apertures in the first and second end plates creates an interconnected void of about 40% to about 70% of the volume of the first and second end plates, respectively.

26. A composite interbody device according to claim 21, wherein the exterior side wall of the central body further comprises a tool receptacle for receiving a insertion tool that can be releasably connected to the interbody device during the implantation of the device between adjacent vertebrae.

27. A composite interbody device according to claim 19, wherein the interior side walls of the first end plate, the first intermediate plate, the central body, the second intermediate plate, and the second end plate form a major aperture passing through interbody device from the superior surface of the first end plate to the inferior surface of the second plate.

28. A composite interbody device according to claim 19, wherein the central body further comprises:
a first screw hole passing from the exterior side wall of the central body to the interior side wall of the central body and towards one of the end plates, wherein the first screw hole is operable to receive a bone screw that connects to one of the vertebral bodies; and
a second screw hole passing from the exterior side wall of the central body to the interior side wall of the central body and towards one of the end plates, wherein the second screw hole is operable to receive a bone screw that connects to one of the vertebral bodies.

29. A composite interbody device according to claim 28, wherein the first screw hole intersects the superior surface of the first end plate and the second screw hole intersects an inferior surface of the second end plate.

30. A composite interbody device according to claim 28, wherein the central body further comprises a receptacle for receiving a back-out plate that is adjacent to the first and second screw holes, and wherein the back-out plate inhibits the bone screws from backing out of the upper and lower vertebral bodies.

31. A composite interbody device according to claim 19, wherein, in the second end plate, at least one of the first array of apertures each pass from the superior surface through the second end plate to the inferior surface.

* * * * *